United States Patent [19]
Suzuki et al.

[11] Patent Number: 6,069,097
[45] Date of Patent: May 30, 2000

[54] COMPOSITE ELASTIC MATERIAL HAVING MULTISTAGE ELONGATION CHARACTERISTICS AND METHOD OF MANUFACTURING THE SAME

[75] Inventors: Migaku Suzuki, Kanagawa; Hiroaki Fukui, Kawaguchi, both of Japan

[73] Assignee: Paragon Trade Brands, Inc., Norcross, Ga.

[21] Appl. No.: 08/860,700

[22] PCT Filed: Jan. 12, 1996

[86] PCT No.: PCT/JP96/00041

§ 371 Date: Sep. 16, 1997

§ 102(e) Date: Sep. 16, 1997

[87] PCT Pub. No.: WO96/21760

PCT Pub. Date: Jul. 18, 1996

[30] Foreign Application Priority Data

Jan. 12, 1995 [JP] Japan ...................................... 7-002973
Aug. 18, 1995 [JP] Japan ...................................... 7-210600

[51] Int. Cl.[7] ............................. D04H 3/16; A61F 13/56; B32B 5/04; B32B 25/10
[52] U.S. Cl. .......................... 442/328; 442/105; 442/329; 442/361; 442/364; 442/381; 428/198
[58] Field of Search ..................................... 442/328, 329, 442/105, 361, 364, 381; 428/198

[56] References Cited

U.S. PATENT DOCUMENTS

| | | | |
|---|---|---|---|
| 4,652,487 | 3/1987 | Morman | 428/138 |
| 4,657,802 | 4/1987 | Morman | 428/152 |
| 4,663,220 | 5/1987 | Wisneski et al. | 428/221 |
| 4,720,415 | 1/1988 | Vander Wielen et al. | 428/152 |
| 5,306,545 | 4/1994 | Shirayanagi et al. | 428/198 |
| 5,422,172 | 6/1995 | Wu | 442/328 X |
| 5,503,908 | 4/1996 | Faass | 442/328 X |
| 5,576,090 | 11/1996 | Suzuki | 428/152 |
| 5,773,374 | 6/1998 | Wood et al. | 442/328 |

FOREIGN PATENT DOCUMENTS

| | | |
|---|---|---|
| 62-028456 | 2/1987 | Japan . |
| 62-033889A | 2/1987 | Japan . |
| 62-084143A | 4/1987 | Japan . |
| 89024625 | 5/1989 | Japan . |
| 91080907 | 12/1991 | Japan . |
| 04281059A | 10/1992 | Japan . |
| 05171556 | 7/1993 | Japan . |
| 05222601A | 8/1993 | Japan . |
| 07252762 | 10/1995 | Japan . |
| WO 95/19258 | 7/1995 | WIPO . |

OTHER PUBLICATIONS

JP 47–29673 (Nov. 1972) English Translation of the Entire Document.

*Primary Examiner*—Daniel Zirker
*Attorney, Agent, or Firm*—Hunton & Williams

[57] ABSTRACT

A composite elastic material comprises a non-woven fabric secured to an elastic member. The non-woven fabric is elastically stretchable by about 100% or more. The sheet-like elastic member has an elastic recovery of about 60% or more and a break-down elasticity of about 200% or more. The elastic member and the non-woven fabric are secured together at a plurality of points in the stretchable direction of the non-woven fabric. The composite elastic material has multiple-stage elongation characteristics including a first stress lowering point caused by changes in the structure of the non-woven fabric, and a second stress lowering point occurring at an elongation larger than that of the first stress lowering point, caused by the fracturing of the sheet-like elastic member. The elastic material clearly shows a breakdown point when stretched, and increases the flexibility of designing various products.

31 Claims, 27 Drawing Sheets

STRETCHING DIRECTION

STRETCHING DIRECTION

STRETCHING DIRECTION

COMPOSITE ELASTIC MATERIAL HAVING MULTISTAGE ELONGATION CHARACTERISTICS AND METHOD OF MANUFACTURING THE SAME

FIELD OF THE INVENTION

The present invention relates to a composite elastic material comprising a non-woven fabric and an elastic sheet, which has different stretch-recovery properties according to the degree of elongation. The composite elastic material can be advantageously used as an elastic material which directly contacts the skin of the human body, such as an elastic material provided for the lumbar region or the crotch region of sanitary articles such as baby and adult diapers, and the sleeve portion of a medical gown.

PRIOR ART

Elastic members are used in disposable goods such as medical articles and hygienic articles in order to improve the fitness around the human body. When used with baby diapering articles, an elastic material is often used in conjunction with a non-woven fabric. In a composite comprising a non-woven fabric and an elastic sheet, elastic functions are performed by the elastic sheet while the non-woven fabric improves the surface condition of the composite and reinforces the elastic sheet.

Typical examples of such composite elastic materials include a three-layer composite elastic material which is referred to as S.M.S. (spun-bond/melt-blown/spun-bond) made by Kimberly, U.S.A., as disclosed in JPA Nos. 84143/87, 28456/87 and 33889/87. Such composite elastic material is manufactured according to a system which is referred to as S.B.L. (Stretched Bonding Laminate), which comprises stretching an elastic sheet, laminating the sheet to a non-woven fabric in an elongated state, and thereafter loosening the laminate. According to this method of manufacture, the composite elastic material is neither elongated beyond that in a usual application state nor fractured. However, the system has several drawbacks for high velocity commercial production, notable among them the necessity of using more non-woven fabric than is needed and a completed article of relatively large bulk.

JPA No. 281059/92, on the other hand, discloses a system in which fiber is directly entangled with an elastic net. This system however has high manufacturing costs. In order to reduce the manufacturing costs, JPA No. 222601/93 attempts to use an elongated non-woven fabric in order to provide a composite elastic material having a channel structure. In JP '601, the non-woven fabric is line-bonded to an elastic film.

A prior composite elastic material as mentioned above is capable of being elongated in a relatively large range. However, the breaking point is undefined, which is a critical problem. Furthermore, when worn, the composite elastic material may break by excessive or repeated elongation, the degree to which is also undefined.

These and other drawbacks of the prior art are sought to be overcome by the composite elastic material of the preferred embodiments.

SUMMARY OF THE INVENTION

It is an object of the present invention to provide a composite non-woven fabric and elastic sheet which are easily produced and relatively inexpensive.

Another object of the present invention is to provide an absorbent product manufactured from the composite elastic material.

According to the present invention, the composite elastic material having a multiple-stage elongation property comprises: a non-woven fabric which is stretchable along at least one direction and has a break-down elasticity along said direction of 100% or more; and a sheet-like elastic member having an elastic recovery of 60% or more and a breakdown elasticity of 200% or more; said non-woven fabric and said elastic member being secured together at a plurality of locations, so that said composite elastic material has a first stress lowering point caused by changes of structure of said non-woven fabric while being stretched along said direction, and a second stress lowering point occurring at an elongation larger than said first stress lowering point, said second stress lowering point caused by break-down of said sheet-like elastic member.

The composite elastic material of the present invention is uniaxially elongated with an approximate constant increase of stress until the composite elastic material reaches a first elongation point. When the composite elastic material is further uniaxially elongated, the stress rapidly lowers until it reaches a second elongation point, at which it fractures.

The composite non-woven fabric is heated and drawn at the softening point temperature of a thermoplastic jointing component which is one of the constituents of the composite non-woven fabric, but below the temperature break-down point of a skeleton component. The composite non-woven fabric comprises a fibrous thermoplastic jointing component and the skeleton component which has a relatively high heat-stability. Since the composite non-woven fabric has an elongating property of 100% or more in one direction, and has a pleasant feeling, the composite elastic material is particularly suitable for use as an elastic material in undergarments or sanitary articles.

In order to provide a structure having an easily elongatable property while maintaining the morphology and the properties of a non-woven fabric, it is necessary to reorient constituent fibers while maintaining the warp-weft bond thereof. In order to satisfy this condition, the present invention includes a method by which the jointing component is plasticized to reorient the fibers so that the spatial orientation between the constituent fibers is changed while passing through a drawing apparatus.

DETAILED DESCRIPTION OF THE PREFERRED EMBODIMENTS

Figure 1:
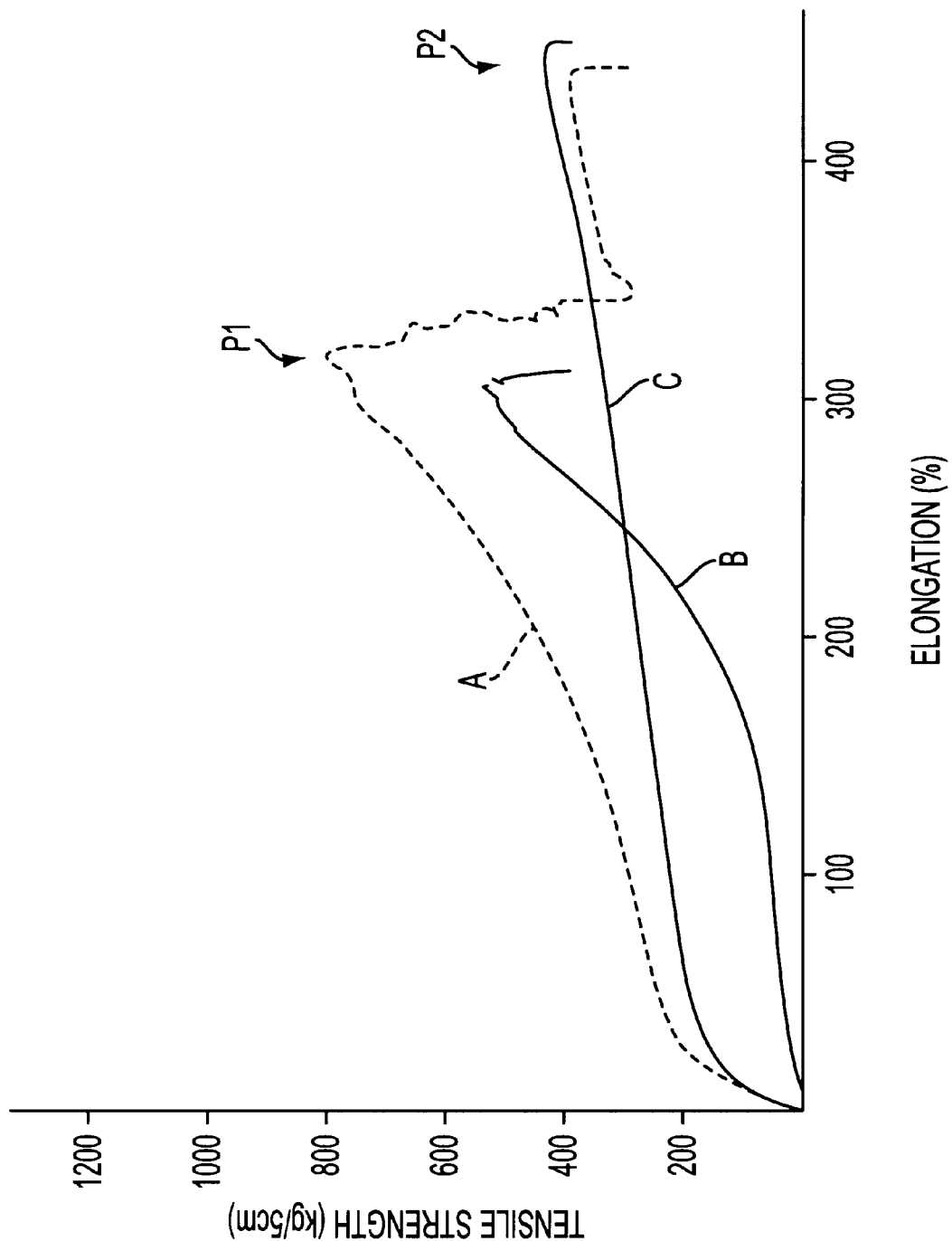
FIG. 1 shows S—S curves of the composite elastic material of a first preferred embodiment of the present invention, a non-woven fabric and an elastic sheet, respectively, while each was elongated until broken.

As a typical embodiment, the composite elastic material of the present invention will be described first with reference to FIG. 1.

The composite elastic material of the first preferred embodiment comprises a non-woven fabric and an elastic material sheet joined by discontinuous adhesive dots extending approximately perpendicular to the direction of elongation. The non-woven fabric is preferably a water entangled polyester carded web having a machine/cross direction elongation ratio of 1/4 and a basis weight of 20 g/cm². The elastic member is preferably a film having a thickness of 40 $\mu$m. The film is obtained by die-extruding a compound comprising 80 parts of S.E.B.S. resin and 20 parts of E.V.A. Curve (A) in FIG. 1 shows the stress-strain relationship (S—S curve) of the composite elastic material when the composite elastic material was elongated in the cross direction at a constant speed. Curve (B) shows an S—S curve of the non-woven fabric alone, while curve (C) shows the S—S curve of the elastic material sheet alone.

In the composite curve (C), elongation occurs rapidly without too much stress at first. Thereafter, the stress increases as it approaches the breaking point of the non-woven fabric. The stress rapidly lowers when it reaches the breaking point of the non-woven fabric. This first inflection point (P1) is the breaking point of the non-woven fabric. The stress produced by yet further elongation thereafter approximates the S—S curve of the elastic sheet itself. Then, the composite elastic material completely fractures when the stress reaches the second inflection point (P2).

Thus, the composite elastic material of the present invention has two stress-lowering points (P1) and (P2) when elongated in a predetermined direction. The first stress-lowering point (P1) occurs when the non-woven fabric is elongated over the elongation limit thereof, while the second stress-lowering point (P2) occurs at the breaking of the elastic sheet.

The composite elastic material thus has multistage elongation properties and can be used for various purposes, including but not limited to, a component of a medical or sanitary article or as the waist gather of a diaper. When used as an elastic waist gather, the composite expands without reaching the breaking point of both the non-woven and the elastic element. That is, when the composite elastic material is subjected to extensive elongation, the non-woven fabric fractures, and the stress rapidly decreases. Since, however, the elastic sheet is not fractured, further elongation will be sustained until the elastic sheet reaches the breaking point.

The non-woven fabric of the composite elastic material may preferably be elongated along at least one axis by about 100% or more, and preferably by about 150% or more. If the elongation percentage is less than about 100%, the utility of the composite is lowered. Further, the elastic sheet preferably has an elastic recovery of about 60% or more and an elongation before breaking of about 200% or more, preferably about 250% or more. If the elastic recovery is less than about 60% and/or the elongation percentage before breaking is less than about 200%, the elastic property is diminished.

The difference between the elongation percentage before breaking of the non-woven fabric and that of the elastic sheet should preferably be as large as practicably possible. The difference between the elongation percentage before breaking of the non-woven fabric and that of the elastic sheet corresponds to the difference between the first stress-lowering point and the second stress-lowering point. Preferably, the difference is about 50% or more. Most preferably, the difference is about 100% or more.

The simplest structure of the composite elastic material is a two-layer structure in which a single non-woven fabric is bonded to a single elastic sheet. Alternatively, the composite elastic material may be three layers, in which one elastic sheet is interposed between two layers of non-woven fabric, each of the layers comprising one or more non-woven fabric. Still further yet, the composite elastic material may be four-layers having two elastic sheets, each of which have a non-woven fabric bonded to one side thereof and joined to one another along their exposed elastic surfaces.

By properly selecting the following conditions, the functions of the elastic material may be improved:

(1) Using the combined elongation property of a composite non-woven and elastic material;
(2) Using a water entangled non-woven fabric having a two-stage elongation wherein the stress is elevated beyond a certain elongation;
(3) Bonding the composite in an approximately perpendicular direction to the direction of elongation so as not to cause a resistance to the elongation; and
(4) Positioning the bond sites on either side of the elastic sheet so as not to overlap with bond sites on the other side of the elastic sheet.

According to the foregoing conditions, a composite elastic material is obtained which has improved elongation properties, a low residual strain, and exhibits excellent stretch recovery.

Figure 2:
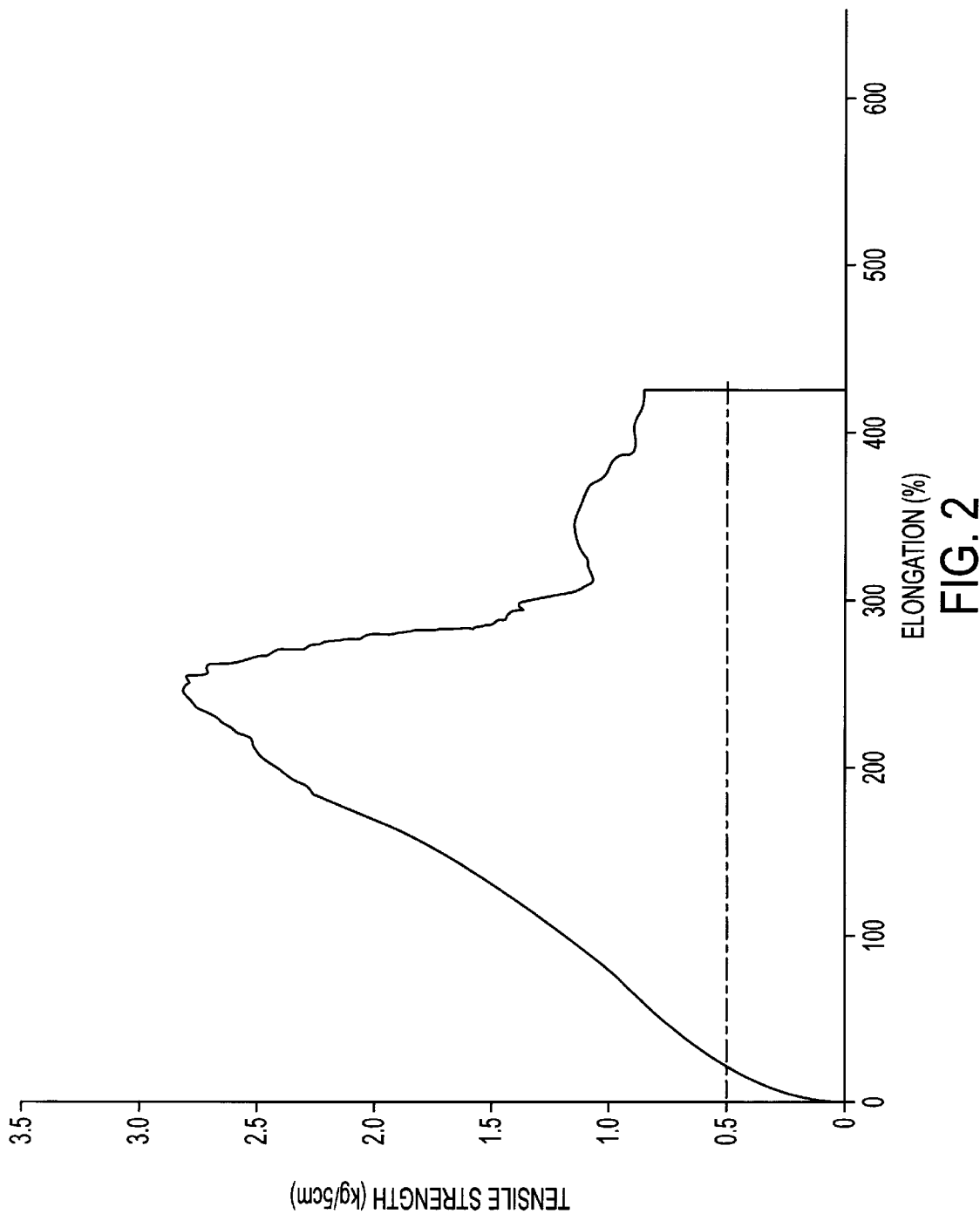
FIG. 2 shows an S—S curve of the composite elastic material of the present invention which was not predrawn, and then elongated until being broken.

FIG. 2 shows an S—S curve of a composite elastic material which comprises a non-woven fabric and an elastic sheet similar to that described above. The composite elastic material of FIG. 2 was continuously elongated at a constant velocity until it fractured. The stress was increased until the elongation percentage approached nearly 250%. At about that point, the non-woven fabric broke and the stress decreased rapidly despite increasing elongation. The composite elastic material as shown in FIG. 2 was pre-drawn. This produces a structure in which the initial elongation and elastic modulus are lowered and the composite elastic material can be easily elongated. For example, through such a predrawing process, when the elongation percentage is about 30%, the stress is lowered to 500 g/5 cm or less.

Figure 3:
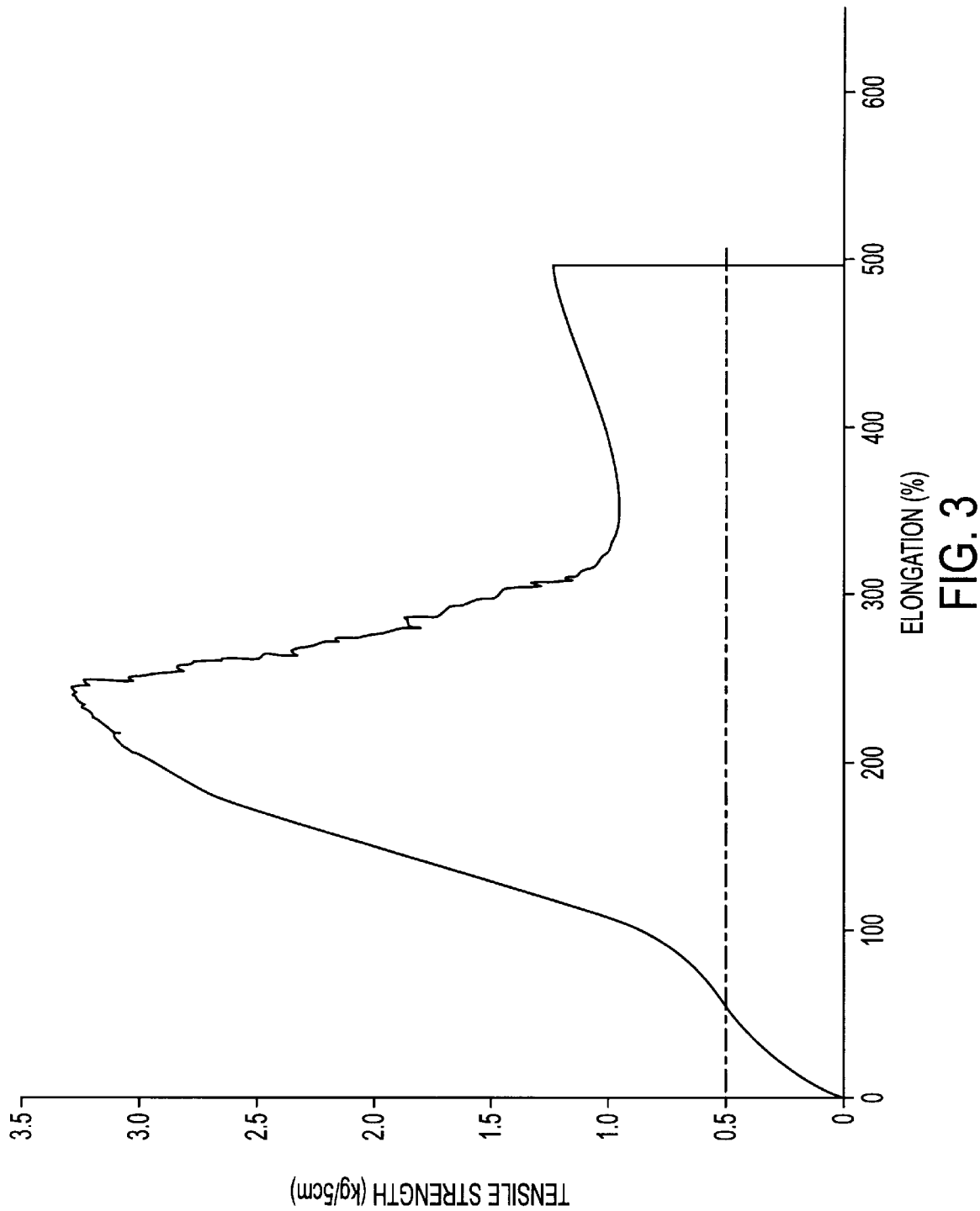
FIG. 3 shows an S—S curve of the composite elastic material of the present invention which was predrawn to 75%, and then elongated until broken.
Figure 4:
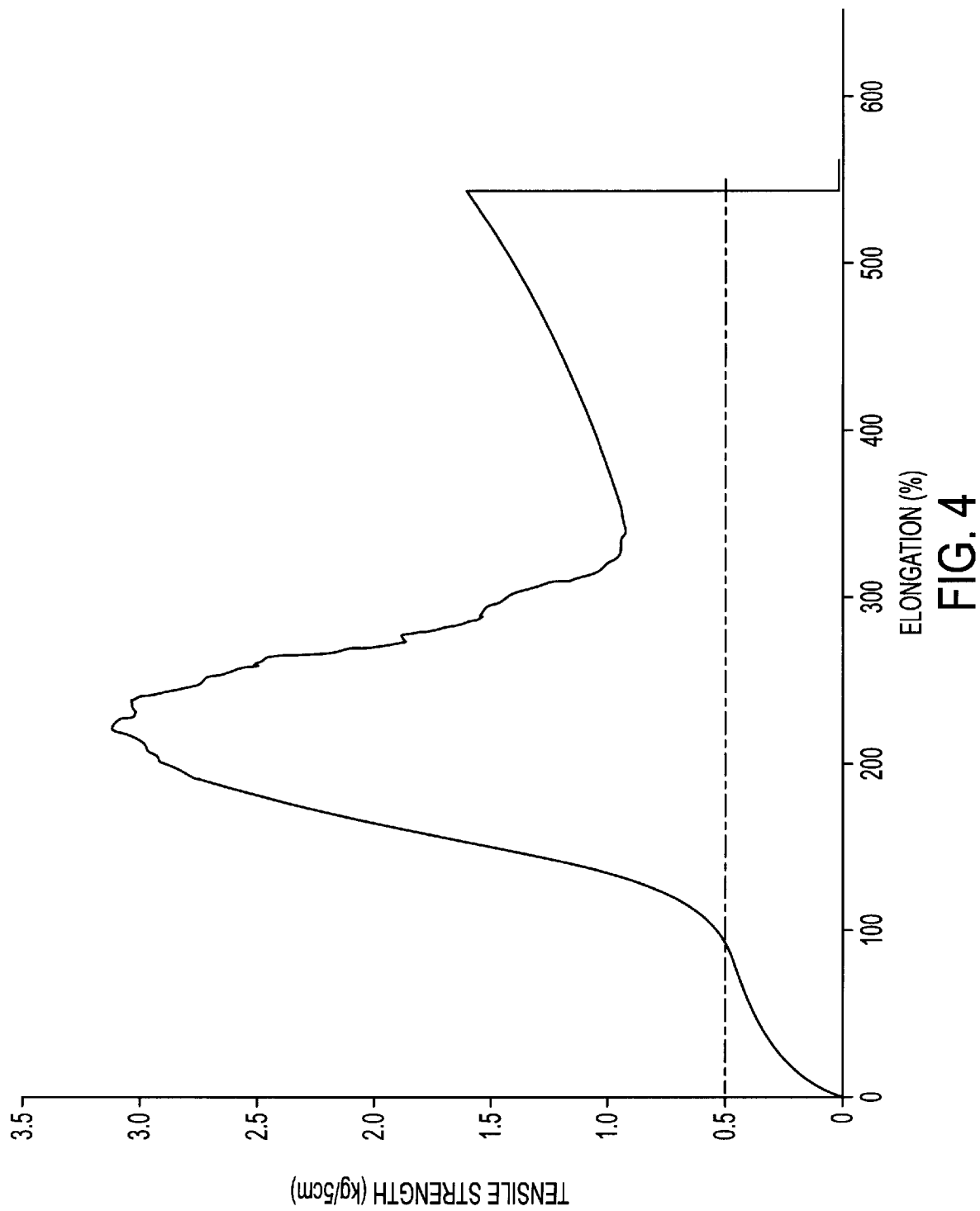
FIG. 4 shows an S—S curve of a composite elastic material of the present invention which was predrawn to 100%, and then elongated until broken.
Figure 5:
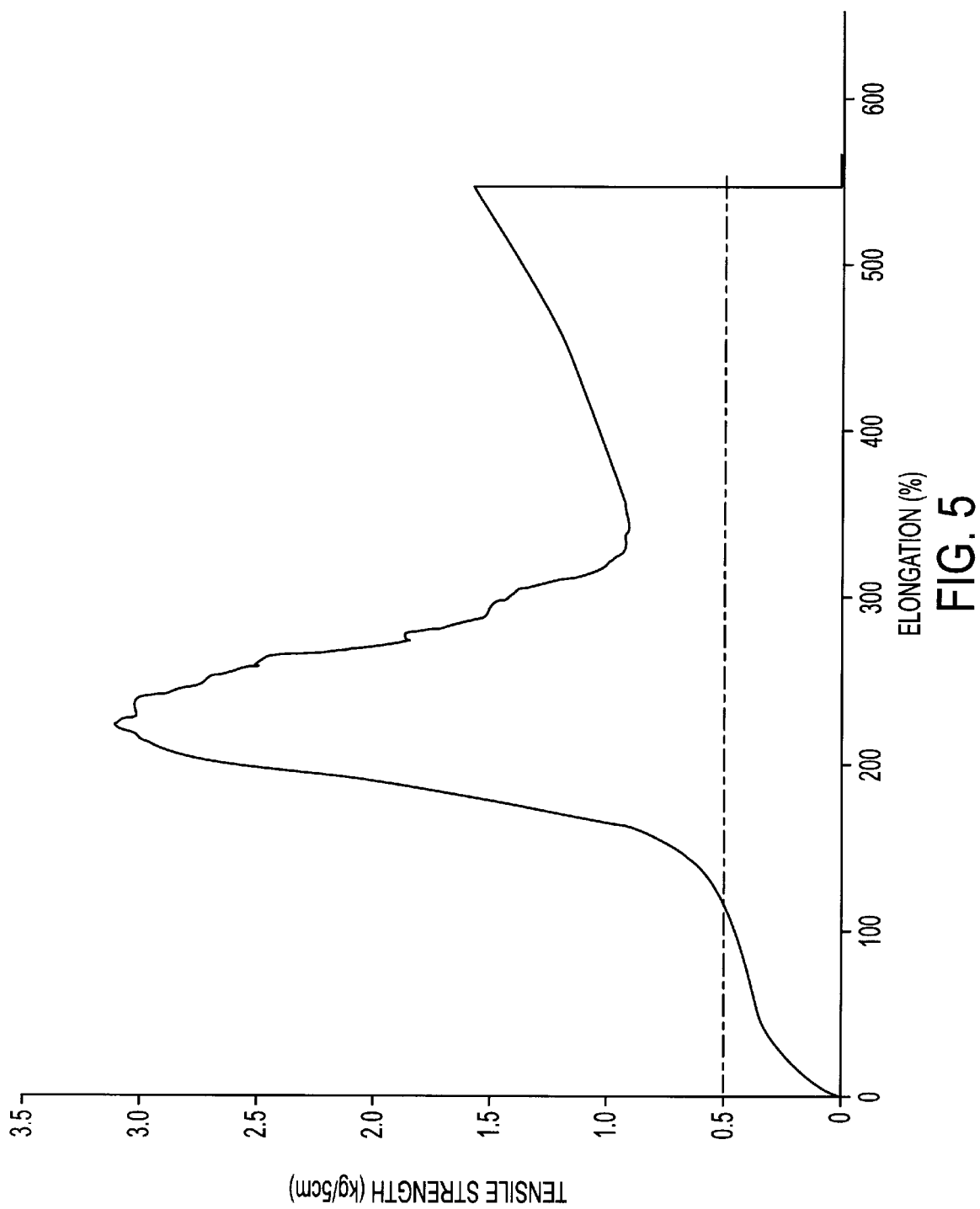
FIG. 5 shows an S—S curve of a composite elastic material of the present invention which was predrawn to 150%, and then elongated until broken.

FIGS. 3, 4 and 5 show S—S curves of composite elastic materials subjected to predrawing of about 75% (which corresponds to about 30% of the elongation percentage after breaking of a non-woven fabric), about 100% (which corresponds to about 40% of the elongation percentage after breaking thereof), and about 150% (which corresponds to about 60% of the elongation percentage after breaking thereof), respectively. This predrawing process is carried out preferably in the range of about 30% to 80% of the elongation limit of a non-woven fabric. If the predrawing percentage is about 30% or less, the predrawing is ineffective, while if the predrawing percentage is about 80% or more, breaking may occur.

Figure 6:
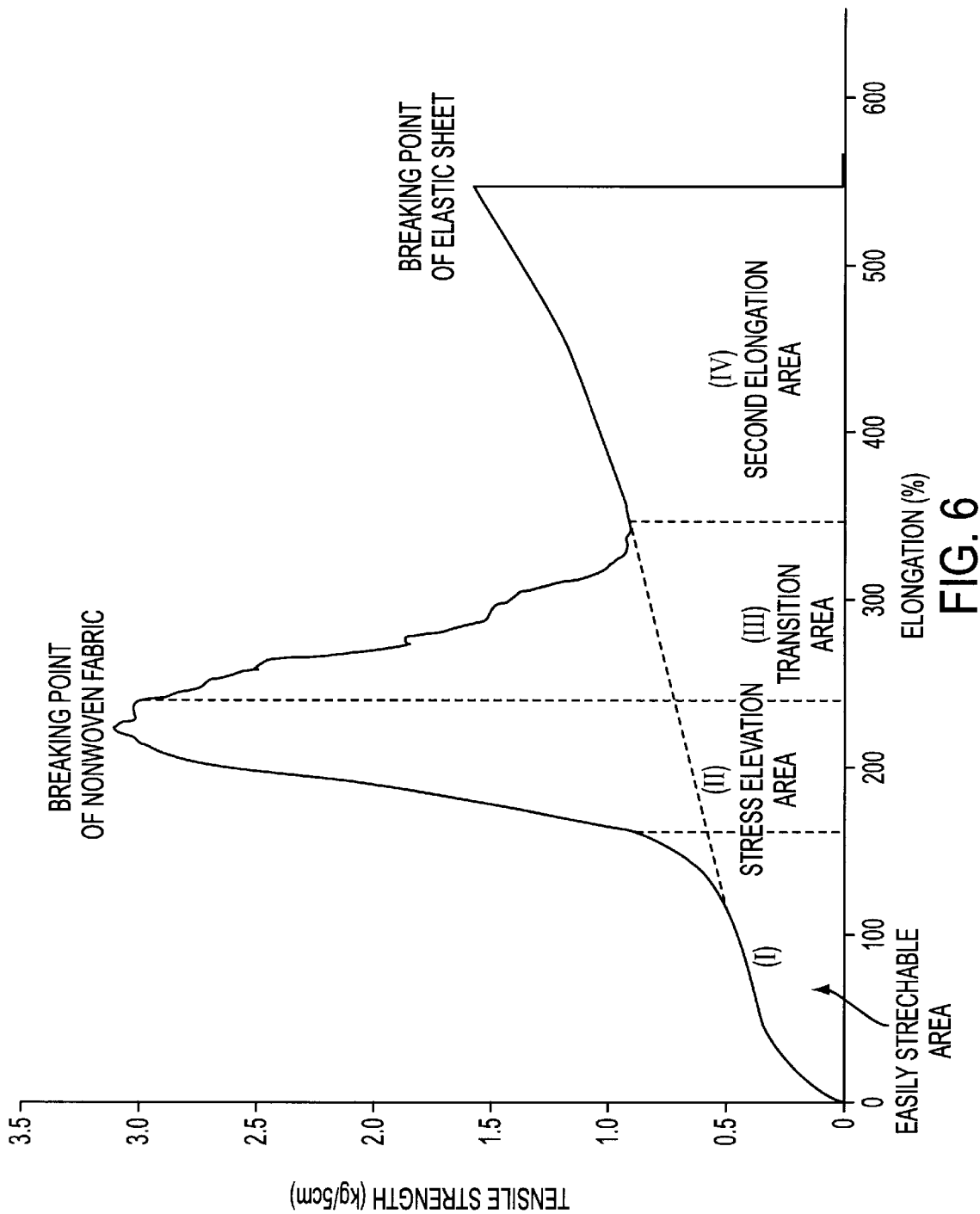
FIG. 6 is a graph (similar to FIG. 5) showing four different areas of the elastic property, which represent on an S—S curve a sample of composite elastic material of the present invention which was predrawn to 150%, and then elongated until broken.

Another composite elastic material is predrawn to exhibit a characteristic S—S curve as in FIG. 6. Area (I) is easily stretchable such that the stress at the point of an elongation percentage of 30% is 500 g/0.5 cm or less. In area (II), the stress rapidly increased as a result of resistance of the transition from a first stress-lowering point to a second stretchable area. The second elongation area (IV) begins with a second stress-lowering point, but not before going through transition area (III).

A composite elastic material having an S—S curve as mentioned above may be applied to, for example, a waist band of an absorbent product. Such a diaper waist band has a signal or stopping function in the event of impending breakage of the non-woven fabric, and holding ability even if the non-woven breaks.

The change of S—S properties before and after predrawing results from a systematic change to the non-woven fabric itself, and/or the bond sites of the non-woven fabric and the elastic sheet. This change provides an improved elastic material when the composite elastic material is used for various purposes. However, whether predrawn or not, the composite elastic material exhibits improved elastic properties when elongated less than the first stress-lowering point.

Figure 7:
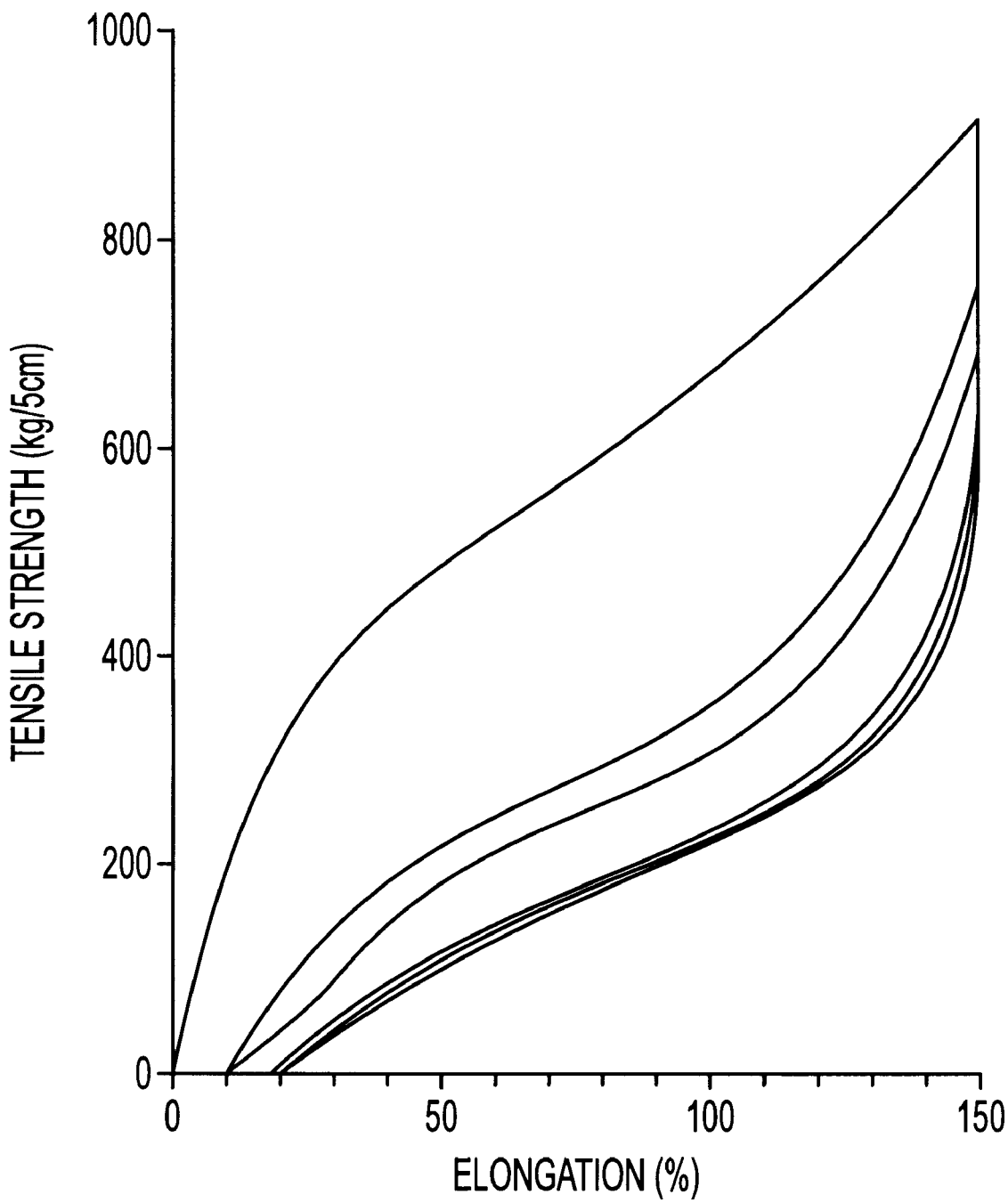
FIG. 7 shows an S—S curve of a composite elastic material of the present invention, when elongated to 150%, and thereafter allowed to recover.
Figure 8:
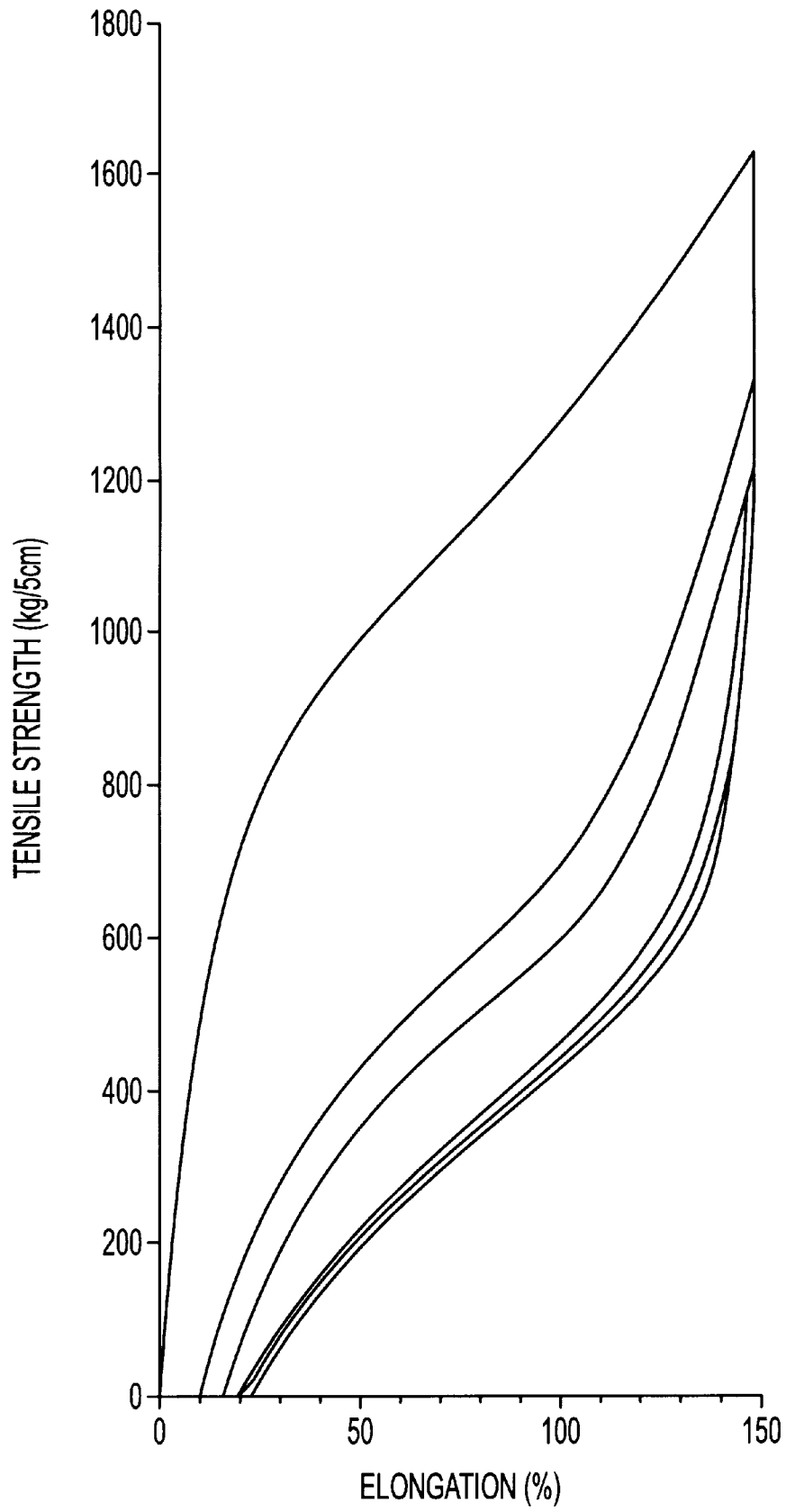
FIG. 8 shows an S—S curve of another composite elastic material of the present invention, when elongated to 150%, and thereafter allowed to recover.
Figure 9:
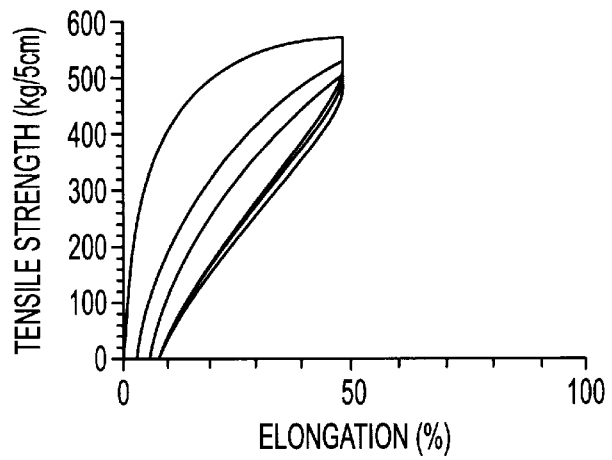
FIG. 9 shows an S—S curve of a composite elastic material of the present invention, when elongated to 50%, and thereafter allowed to recover.
Figure 10:
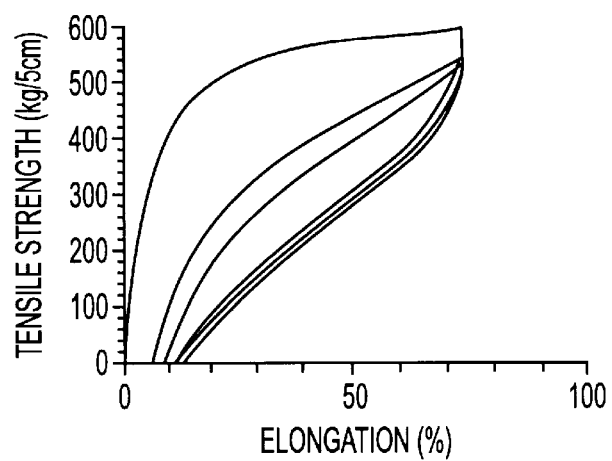
FIG. 10 shows an S—S curve of a composite elastic material of the present invention, when elongated to 75%, and thereafter allowed to recover.
Figure 11:
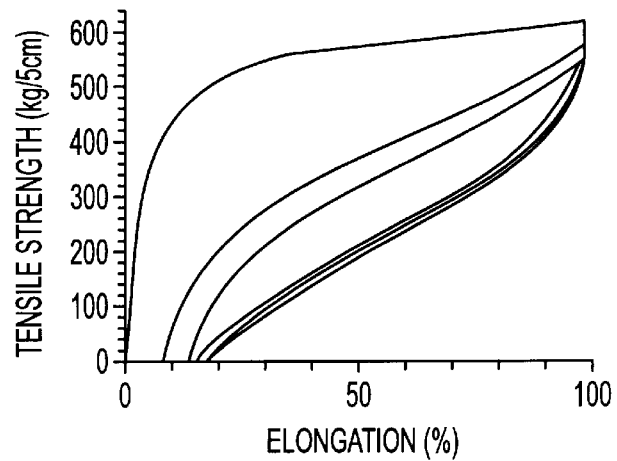
FIG. 11 shows an S—S curve of a composite elastic material of the present invention, when elongated to 100%, and thereafter allowed to recover.
Figure 12:
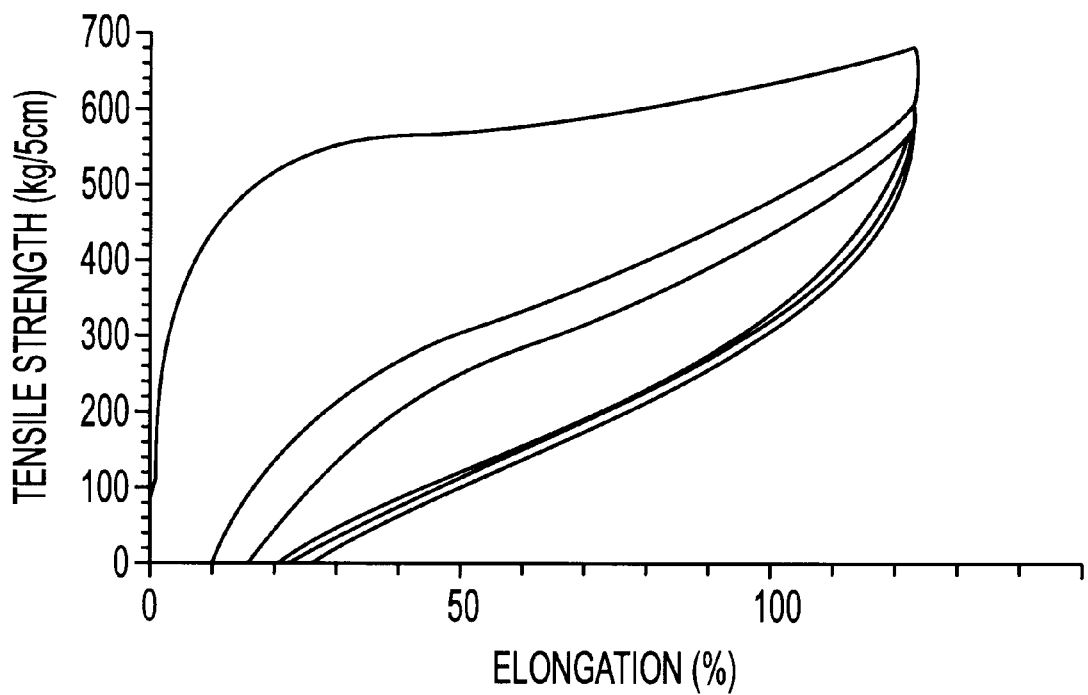
FIG. 12 shows an S—S curve of a composite elastic material of the present invention, when elongated to 120%, and thereafter allowed to recover.
Figure 13:
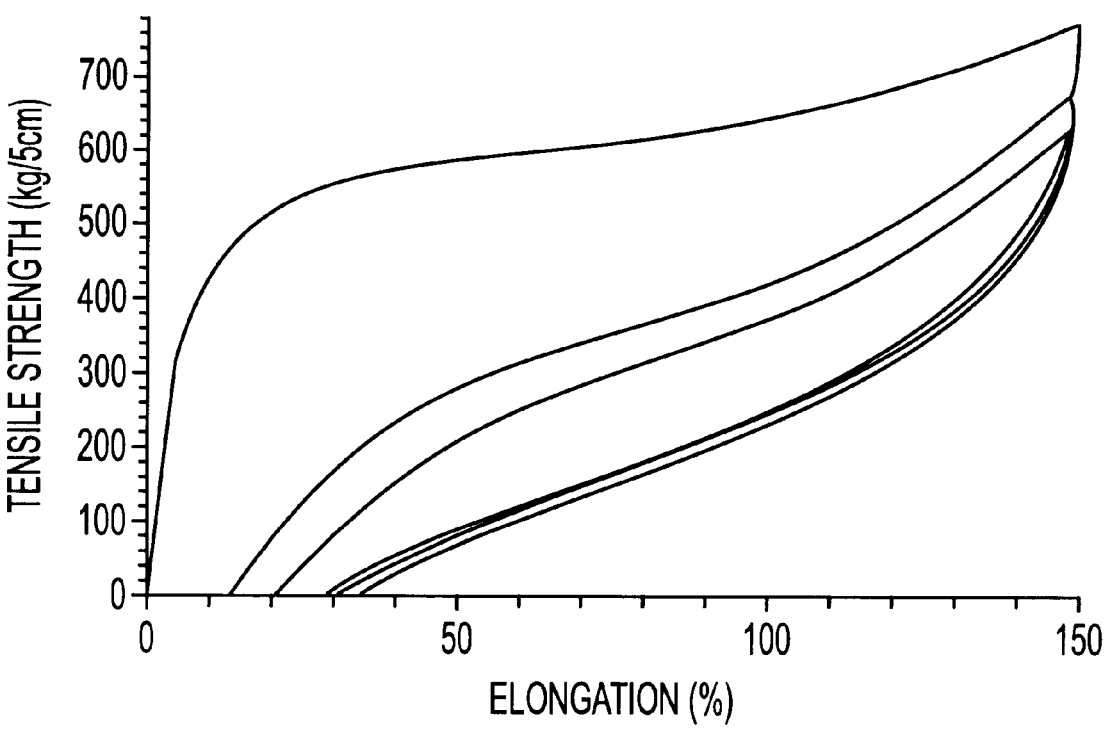
FIG. 13 shows an S—S curve of a composite elastic material of the present invention, when elongated to 150%, and thereafter allowed to recover.

FIGS. 7 and 8 show an S—S curve of typical two layer composite elastic bodies of the present invention elongated 150%, which corresponds in some cases to the elongation after breaking a non-woven fabric. These composite elastic bodies show a relatively high stress when first elongated, since the structural change of the elongation of two materials comprising the non-woven fabric and the elastic sheet occurs virtually simultaneously. However, when the composite elastic bodies are further elongated, the resistance rapidly decreases and the elastic properties are revealed because the non-woven fabrics have been pre-drawn. This phenomena is referred to as "elongation activation" in the present specification.

FIGS. 9–13 show S—S curves of composite elastic materials of further preferred embodiments when elongated to 50%, 75%, 100%, 120%, 150%, respectively, and then allowed to recover. When such materials were worn, the materials are stretchable so as to correspond to the motion of the body, and a flexible fitting-structure is obtained.

The elongation activation preferably naturally occurs when putting on or wearing the product incorporating the composite elastic material. Alternatively, elongation activation occurs by predrawing during manufacturing the product. The elongation activation may be accomplished by widening and elongating a composite elastic material using a simple belt or pin tenter apparatus or using a corrugated roll or ear roll to provide a partial elongation. It is necessary to ensure that the surface of the elastic material is not damaged by the non-woven fabric. With respect to a composite elastic material which was previously subjected to such elongation activation, S—S characteristics as shown in FIGS. 7 to 13 for the first elongation activation vanish, and the composite exhibits easy elongatable properties and characteristics from the start.

Desirably, large stress should be avoided for the initial elongation as mentioned above, and resistance rapidly elevates after the elongation percentage passes a certain range. Accordingly, resistance to elongation rapidly increases before the composite elastic material fractures. Moreover, even after repeated stretching, similar elastic properties are maintained. Residual strain is also small, which is important to the composite's fundamental performance.

The numeric representation of these advantageous conditions may be measured and analyzed. Specifically, the composite elastic material is measured at intervals of 5 cm width. The measurement of physical properties as shown below was carried out on the basis of JIS (the Japanese Industrial Standards), which is commonly used in the field. The main points are as follows:

1. Test Samples
    Width: 5 cm
    Length: 15 cm
2. Conditions for Determining S—S curves
    Chuck Space: 10 cm
    Loading Speed: 20 cm/min.
3. Cycle Tests The load-unload operation was repeated three times at an elongation percentage of about 150% to obtain a hysteresis curve thereof. Examples of the load-unload hysteresis curves can be seen in any of the curves of FIGS. 7–13. Stresses at about 30% and at about 100% from the final return point of the hysteresis curve were read. Five minute intervals were provided as a restoration time between each cycle; i.e., First Measuring→5-minute Interval→Second Measuring→5-minute Interval→Third Measuring.

(1) Stress Elongation Percentage of 30%

The initial elongation stress, which corresponds to the force necessary for an initial elongation on wearing, needs to be accurately controlled. Otherwise, too large a stress makes it difficult to elongate the composite in the first instance. Desirably, the stress should be about 1000 g or less, preferably about 800 g or less, and most preferably about 600 g or less.

(2) Stress at Elongation Percentage of 100%

This stress initiates the elongation activation, which varies according to the working condition of an object and the extent to which the object is elongated. Since the composite elastic material of the present invention is intended to be used for relatively high elongations, the stress at an elongation percentage of about 100% is selected as a point of reference. For the elongation activation of a composite elastic material to be initiated, a stress of about 400 g or more is needed at an elongation percentage of 100%. Thus, when the stress exceeds about 400 g or more, and more preferably about 800 g or more, the elongation activation is initiated by the initial elongation.

(3) Strength against Breaking

The strength against breaking is preferably about 400 g or more. However, if increased to about 600 g or more, unexpected breaking may be avoided, since resistance indicative of the elongation limit can be more clearly felt.

When elongation activation was achieved, the measured value of the stress sharply lowered after the elongation activation. For example, when an elongation activation was obtained following about 150% elongation, the stress to elongate the composite elastic material again by about 150% is sharply lowered. Such stress reduction upon subsequent elongation activations is illustrated by the hysteresis curves of FIGS. 7–13. In view of the intended uses of the composite elastic material of the present invention, the lowering of the elongation stress represents an advantageous improvement over the prior art.

When a second S—S curve is determined for a composite elastic material after an elongation activation was achieved following about 150% elongation, the following conditions are observed.

(1) Stress at Elongation Percentage of 30%

The stress preferably is about 500 g or less, desirably about 400 g or less, and most desirably about 300 g or less. By selecting such conditions, even when the composite elastic material is applied to, for example, a baby product, it is possible to avoid excessive expansive forces to install the product.

An important characteristic of the composite of the preferred embodiments is elongation recovery power so that the recovery percentage is high. A structure having a lower residual strain is preferable. Elongation recovery percentage is commonly measured after elongation of about 150% is repeated three times. The recovery percentage represented under such conditions is about 60% or more, preferably about 70% or more.

The elastic sheet for the composite is selected preferably from raw materials which will elongate about 200% or more and have an elongation recovery property of about 60% or more. Examples of materials satisfying these performance criteria include, for example, urethane or rubber latex; styrene elastomer film such as isoprene or butadiene synthetic rubber film, SIS, S.E.B.S., or S.E.P.S.; polyolefin elastomer film; and melt-blown elastomer non-woven fabric such as polyurethane, SIS, or S.E.B.S. The elastic sheets are preferably a film in the form of a net or a melt-blown non-woven fabric comprising a styrene elastomer such as SIS or S.E.B.S. having a good thermal bonding property, and having a blended elastomer.

The non-woven fabric preferably has a large elongation property in the machine direction (MD) and the cross-machine direction (CD). Inevitably, a non-woven fabric having an elongation property in both the MD and CD somewhat sacrifices an elongation property in the CD. Non-woven fabrics having large elongation properties in the CD are commercially available. Examples include non-woven fabrics which are manufactured by water entanglement; non-woven fabrics having open and wide continuous tow fibers; and spun-bond or melt-blown non-wovens in which the fibers are arranged in parallel. The non-wovens to be used in the composite can be roughly classified into the following three groups:

Group 1

A non-woven fabric produced from a card web. The fibers are oriented in the MD and subjected to water entanglement. The ratio of elongation in the MD to the CD (MD/CD ratio) is about 2 or more, preferably about 3 or more. The non-woven is preferably drawn.

Group 2

A non-woven fabric obtained by thermodrawing and parallelizing a spun-bond non-woven fabric, a melt-blown non-woven fabric, or a dry non-woven fabric in which the MD/CD ratio is about 2 or more, preferably about 3 or more, and wherein the fibers are oriented in the MD. In addition, non-wovens manufactured by heating a spun-bond and drawing it to the melting point. The composite fiber has a sheath part formed from an easily meltable polymer such as polyethylene or a PET derivative, and a core portion formed from a thermally stable polymer such as polypropylene or PET. This non-woven fabric is particularly suitable for the present invention, because it is thin, has fibers oriented in parallel, and has virtually no standing fibers.

Group 3

A non-woven fabric chosen from a spun-bonded non-woven fabric, a melt-blown non-woven fabric, or a dry non-woven fabric in which the ratio of MD/CD is about 2 or more, preferably about 3 or more, in which fibers are oriented in the MD and provided with a plurality of fine slits in the MD.

The stretchable property in the MD or CD is desirably about 100% or more, more desirably about 200% or more. Due to such elongation properties of the non-woven fabric, the behavior of the elastic sheet follows the non-woven fabric. Moreover, when the elongation exceeds a certain value, the non-woven fabric resists further elongation.

Figure 14:
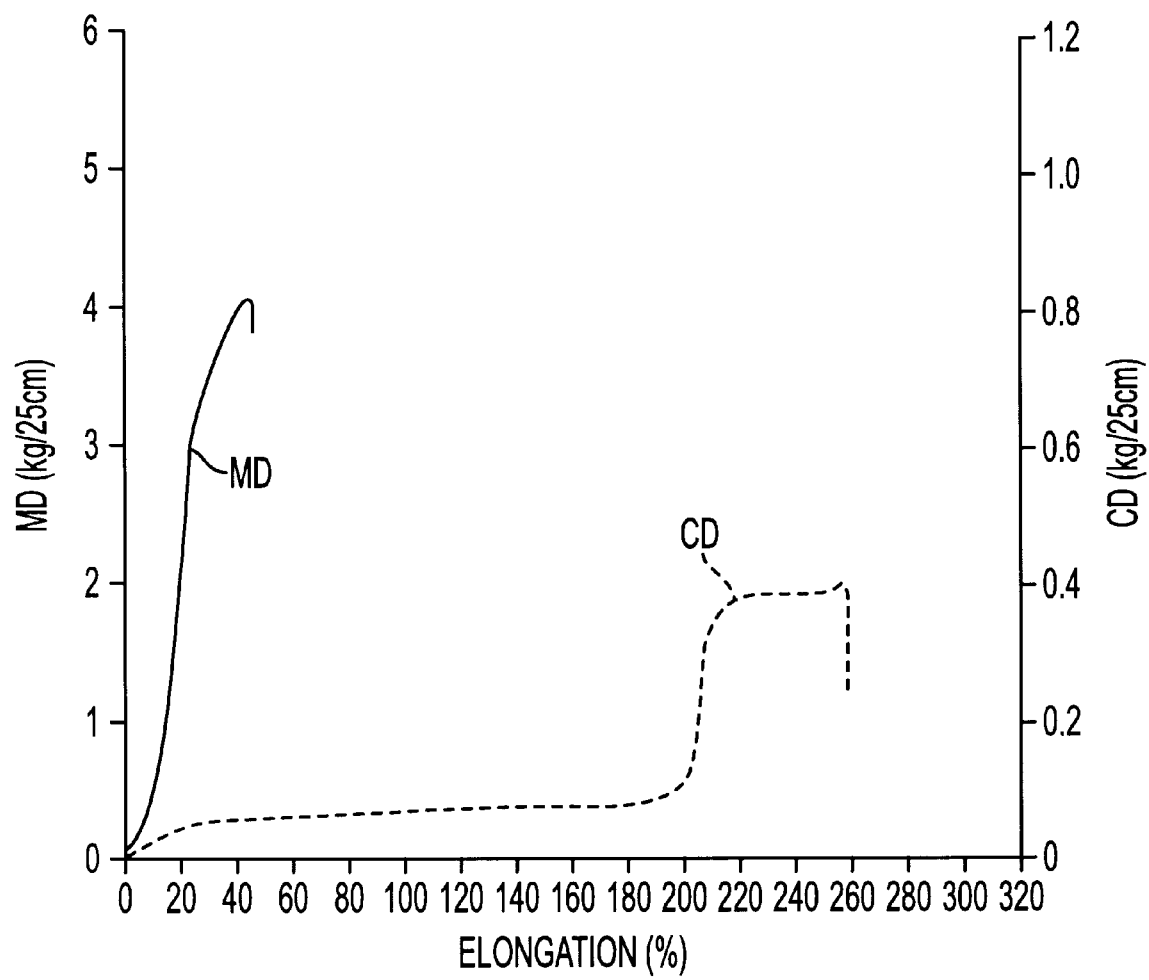
FIG. 14 shows an S—S curve in the MD and CD of a non-woven fabric of the present invention which is water entangled.

One non-woven fabric which is particularly advantageous for the present invention is water entangled non-woven fabric. As shown in FIG. 14, the water entangled non-woven fabric shows little elasticity in the MD, but exhibits large elasticity in the CD when it is elongated to about 200% of its natural length. At this point, the stress sharply elevates, and upon further elongation it breaks (corresponding to an elongation percentage of about 260%). This elevation of stress at the second stage will act as a warning before fracturing. The non-woven fabric is designed so that the stress-elevation point is higher than about 150% elongation.

(2) Selection of Stream Entangling Conditions

Using fine nozzles, the non-woven fabric was jointed at selected areas. For example, the following three-stage nozzles are preferably used:

1 st Step Nozzle Diameter: 0.15 mm
   Nozzle Spacing: 0.5 mm
   Water Pressure: 30 kg/cm$^2$ 2nd Step Nozzle Diameter: 0.15 mm
   Nozzle Spacing: 0.5 mm
   Water Pressure: 50 kg/cm$^2$ 3rd Step Nozzle Diameter: 0.25 mm
   Nozzle Spacing: 1.0 mm
   Water Pressure: 60 kg/cm$^2$ A water entangled non-woven fabric having a striped pattern and elongatable in the MD results.

Another example of a non-woven fabric which can be advantageously used for the present invention is a composite non-woven fabric mentioned in Group 2 above. This non-woven fabric is prepared by drawing a composite non-woven fabric having a jointing component and a skeleton component. The drawing step occurs while heating the non-woven jointing component to about the stabilizing temperature of the skeleton component. The jointing component is thermoplastic, while the skeleton component is relatively thermally stable as compared with the jointing component. A non-woven fabric according to such process is easily stretchable in one direction, and is pleasant to the touch.

In order to maintain the morphology and characteristics of the non-woven fabric, while remaining easily extensible, it is necessary to bond the composite in the machine and cross directions at the same time in order to reorient constituent fibers. In order to satisfy such conditions, the composite non-woven fabric which comprises a jointing component and a skeleton component as mentioned above are heated to plasticize the jointing component. The fluidity of the jointing component fills the space between constituent fibers during the drawing operation so as to reorient the fibers.

Examples for combining the thermoplastic jointing component with the skeleton component are provided below. Both the jointing component and the skeleton component are in the morphology of a filamentous, staple or fibril form fiber. Examples of combinations for the composite non-woven comprising the jointing component (A) and the skeleton component (B) include:

| Types | (1) | (2) | (3) | (4) | (5) | (6) | (7) | (8) |
| --- | --- | --- | --- | --- | --- | --- | --- | --- |
| Component (A) | PE | PE | EVA | PE | SEBS | PE/PET | SEBS | Nylon |
| Component (B) | PP | PET | PP | Nylon | PP | Poly-AN* | Acetate | PET |

*polyacrylontrile

In order to achieve optimum elongation performance, the construction of the web fibers must be carefully chosen in connection with the conditions of the entanglement process. For example, a non-woven fabric having the following construction satisfies the above-mentioned design criteria:

(1) Constitution of the Web

Combining relatively short fibers having a length of approximately 25 mm to 45 mm with relatively long fibers having a length of about 45 mm to 60 mm to form a staple fiber; and combining such fibers to cause a wound-shrink (Kanshuku).

In the above-mentioned combinations, at least the skeleton component (B) is a staple fiber in which fibers are readily oriented by drawing. Most preferably, the fibers of the skeleton component (B) are a continuous filament fiber.

The composite may be either single or double layered. If single layered, the composite comprises a layer of component (A) and a layer of component (B). If double layered, the composite comprises two-layers each of jointing component (A) and skeleton component (B).

The single-layer non-woven fabric is preferably a filament non-woven fabric comprising conjugated fibers of PET (polyester), such as a spun-bond non-woven fabric (ELVES) made by UNITIKA, LTD. The double-layer non-woven fabric, i.e., melt-blown webs having an easily thermoplastic property laminated to both sides of a spun-bond of PET so that the spun-bond is sandwiched between the melt-blown webs, preferably comprises PP (polypropylene) fibril fibers laminated to both sides of an acetate tow. Commonly, it is preferable to arrange the skeleton component (B) as the core, and the jointing component (A) as the surface.

In order to form a structure having the necessary stretchable property while maintaining an adequate strength for users, the constituent fibers are preferably entangled in each other. This may be achieved by a web which is preferably spun-bond wherein the filaments are piled up in a loop state, or a web having high randomness, in which a bundle of tow filaments is opened, widened and laminated. Either of these webs are relatively easily reoriented by thermo-drawing.

A non-woven fabric formed by thermally bonding parallel dry webs of short fibers which are already in an oriented state is not preferred. Likewise, a non-woven fabric in which webs are jointed to each other in machine/cross directions by using a cross-lapper is also not preferred, since the entanglement in the machine/cross direction is too strong.

In order to heat and draw a web so as to reorient the fibers so that the non-woven fabric is easily stretchable in a cross direction, the drawing conditions, i.e., temperature applied to the web, and the heat medium must be properly selected.

It is desirable that between jointing component (A) and a skeleton component (B) which collectively comprise a composite non-woven fabric, the thermoplastic jointing component (A) is plasticized and drawn at a temperature range in which the skeleton component (B) is stable. Commonly, the temperature is in the range of about 900° C. to about 1600° C. For example, the temperature of a composite non-woven fabric comprising a combination of PE/PET is desirably in the range of about 1000° C. to about 1200° C.

The most suitable heating medium is steam and hot water. Drawing in such a heating medium does not cause mutual joints between constituent fibers, and provides and easily stretchable non-woven fabric having a soft finish. The denier of the constituent fibers is lowered by drawing, which contributes to the softening of the material.

Steam or hot water is desirably used as the heating medium by combining hot water with hot air, or by combining steam with hot air. When drawing is carried out in multiple steps, a combination of plural heating media are preferably employed. A heating roller or dry hot air is not a preferred method of heating, because of the danger of mutually thermo-melting constituent fibers of the webs.

If the web is pre-treated by widening it prior to the heated drawing process, a stretchable non-woven fabric having an excellent quality is more easily obtained. In this case, a large widening percentage is not necessary, but rather a widening percentage in the range of about 110% to about 150% is sufficient. Expander rolls or grid gears can be used to widen the web. The widening preferably occurs in air heated to about 700° C. to 800° C. Drawing is then preferably carried out in the presence of saturated steam.

Figure 15:
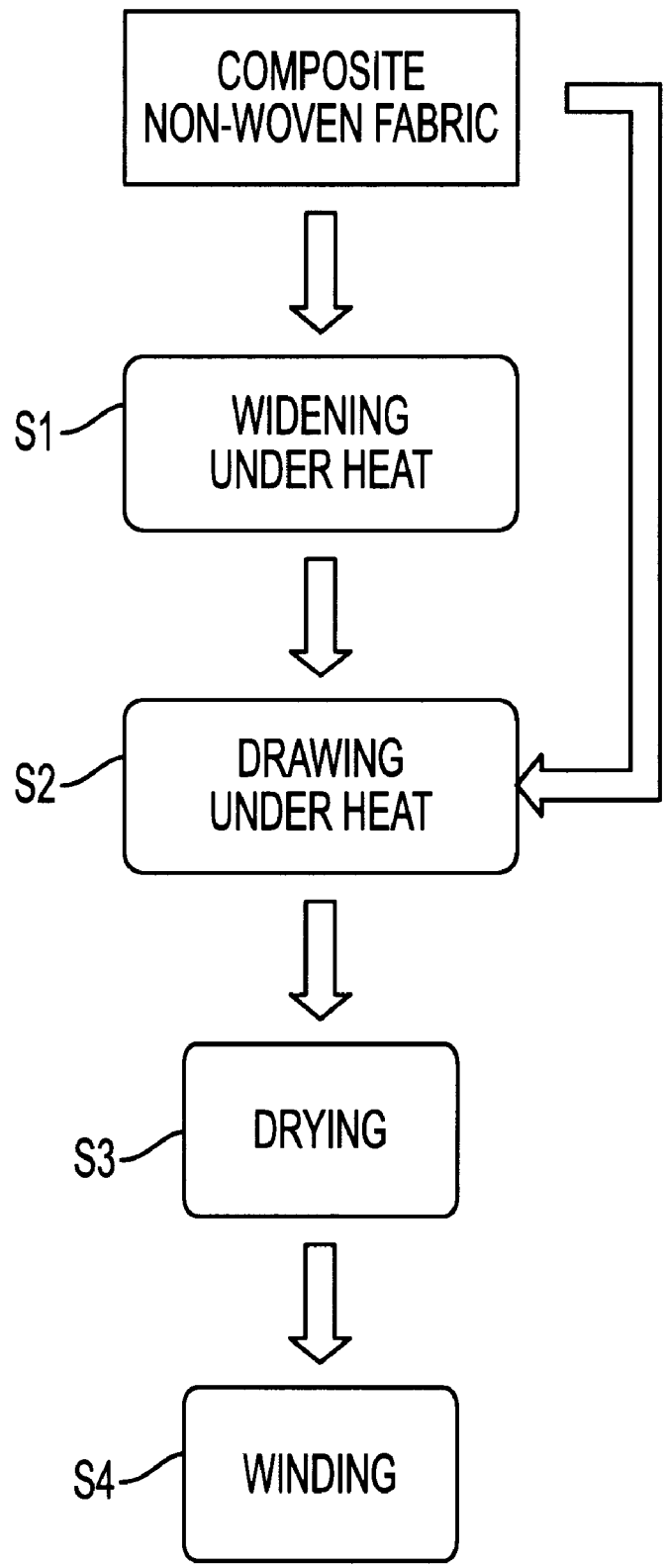
FIG. 15 is a schematic diagram showing an example of the process for manufacturing an elongating non-woven fabric according to the present invention.

FIG. 15 is a flow chart showing one example of a process of manufacturing a web according to the present invention. In FIG. 15, the composite non-woven fabric is first widened in the presence of steam heating (Step S1). Next the web is drawn in the presence of steam in an approximately perpendicular direction to the widening direction (Step S2). Next, the web is dried (Step S3). Finally, the web is wound into a roll (Step S4). As mentioned previously, the widening step is optional and may be omitted altogether, in which case the process proceeds directly to the drawing step (S2).

During the drawing operation, the width of the web tends to shrink, which will often cause wrinkles. If the wrinkles are not preferred, the width can be controlled by using a tenter. On the other hand, however, wrinkles may be desirable. Wrinkles in the machine direction can be controlled to intentionally provide a micro-corrugated structure so as to form a non-woven fabric structure which is more easily stretchable in a cross direction.

Figure 16:
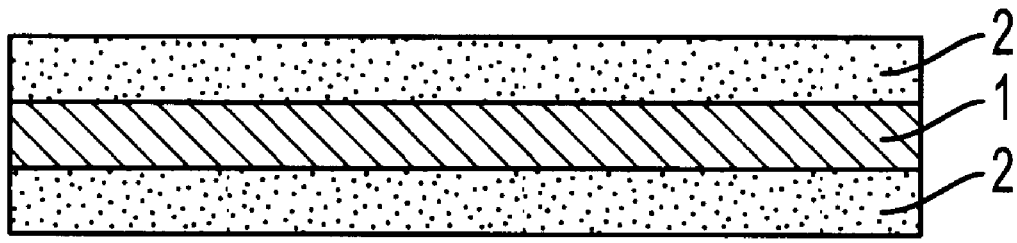
FIG. 16 is a sectional view showing the construction of a composite non-woven fabric of the present invention.
Figure 17:
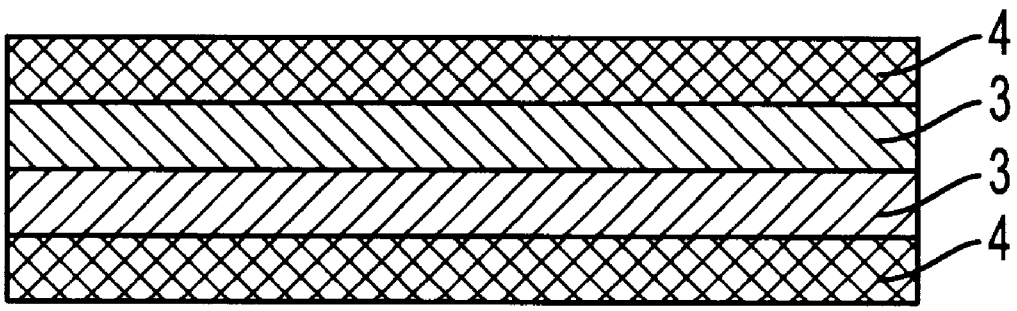
FIG. 17 is a sectional view showing another construction of a composite non-woven fabric of the present invention.

FIG. 16 illustrates one embodiment of a composite non-woven fabric according to the present invention. The composite has two layers of non-woven consisting of PE melt-blown web layers (2) laminated to both sides of a PET spunweb layer (1). Layers (2) form jointing component (A) and layer (1) forms skeleton component (B). As shown in FIG. 17, an alternative structure may be selected. Two PP fiber web layers (4) forming jointing component (A) are laminated to one side of a PET web layer (3) forming skeleton component (B). They are laminated so that the layers (3) of a skeleton component (B) face each other.

Figure 18:
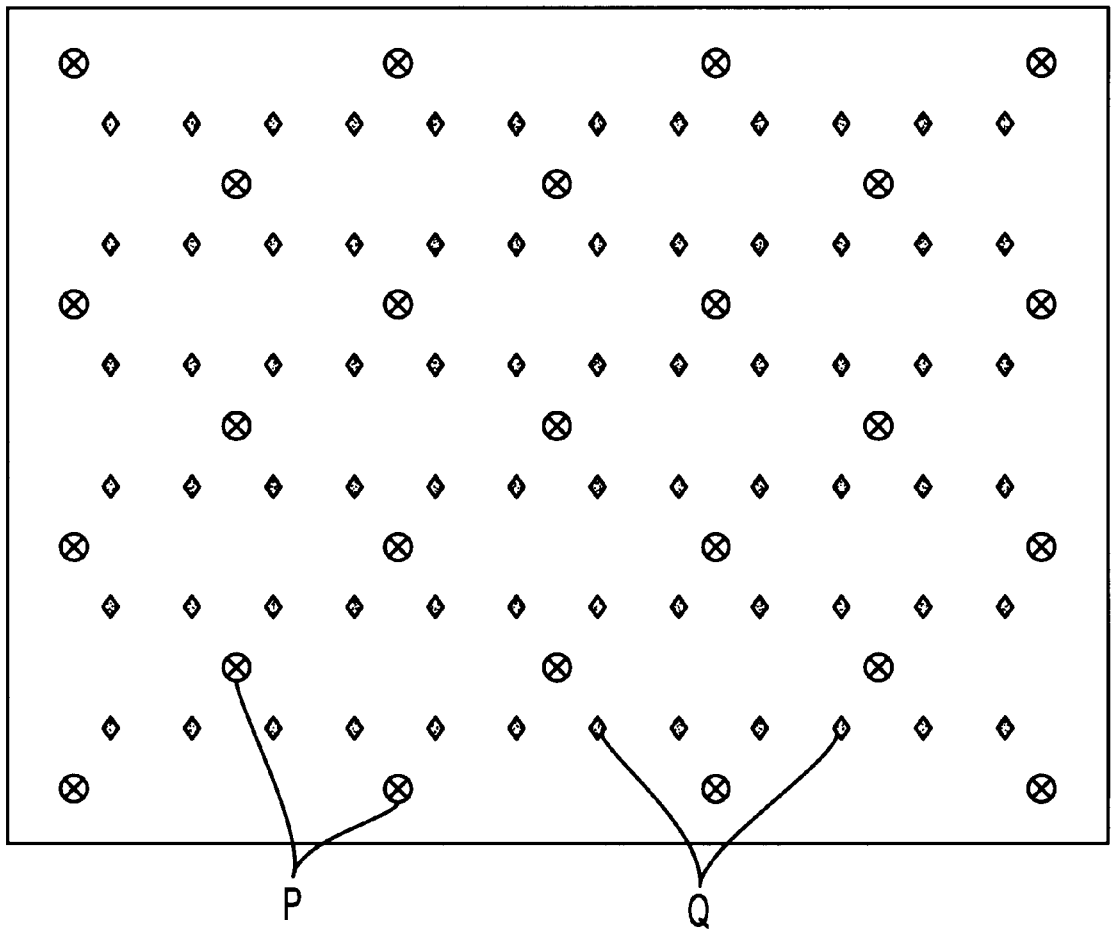
FIG. 18 is a plan view showing the bonding pattern of the composite non-woven fabric of the present invention.

In order that the composite non-woven fabric readily endures the widening and/or drawing steps which are used to reorient the fibers, the layers of the composite non-woven fabric are moderately bonded to each other. In order to increase the homogeneity of the web, the composite non-woven fabric is preferably bonded with many small bond points. If each bond point is too strong, the composite non-woven fabric may not draw properly. In order to avoid this, as shown in FIG. 18, a two-phase bond structure is employed in which two types of bond-points (P) and (Q) are evenly distributed. Bond points (P) and (Q) have different degrees of bonding. In the bond-point (Q), the temperature and pressure are controlled so as to bond merely jointing components (A) to each other, and a jointing component (A) to a skeleton component (B). In the bond point (P), bonding is carried out under temperature and pressure conditions so that the skeleton components (B) also can be bonded to each other.

The non-woven fabric is preferably bonded to either or both of the surfaces of an elastic sheet. In this bond system, the following factors are important in that they effect the performance of the resultant composite elastic bodies:

(1) Aligning and bonding the elongatable direction of a non-woven fabric to correspond with that of the elastic sheet;

(2) Using a bonding pattern in which the bond sites do not impede the elongation of composite elastic bodies, and using as few and as small as possible bond points along the elongation direction; distributing the bond points in the range of about 900–±100 to the elongation direction of a non-woven fabric; and (3) When a non-woven fabric is bonded to both surfaces of an elastic sheet, adjusting the bond sites between one non-woven fabric and one elastic sheet and between the other non-woven fabric and the other elastic sheet so that they are not coincident.

Figure 19:
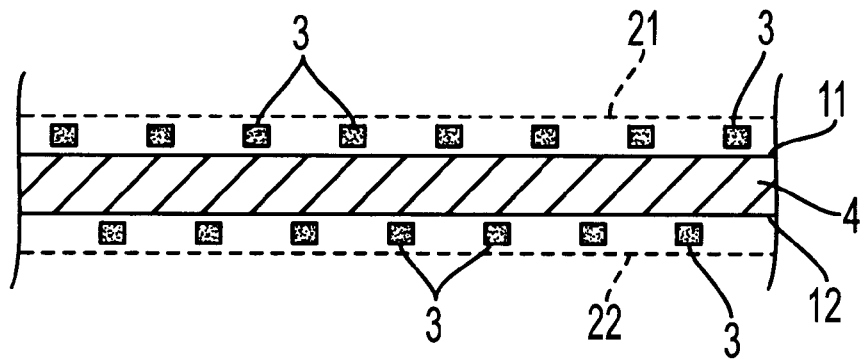
FIG. 19 is a schematic sectional view showing an arrangement of the elastic material sheet and the non-woven fabric of the present invention.
Figure 20:
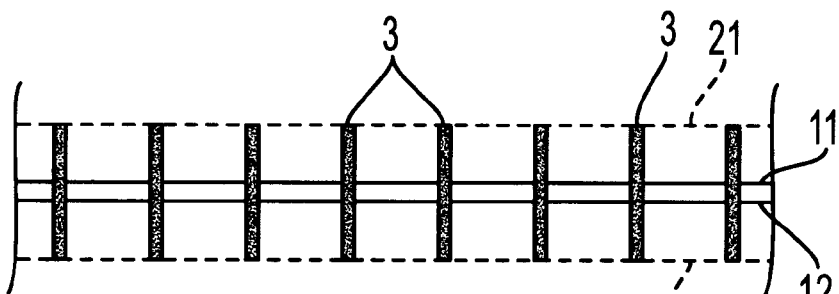
FIG. 20 is a schematic sectional view showing another arrangement of the elastic material sheet and the non-woven fabric of the present invention.
Figure 21:
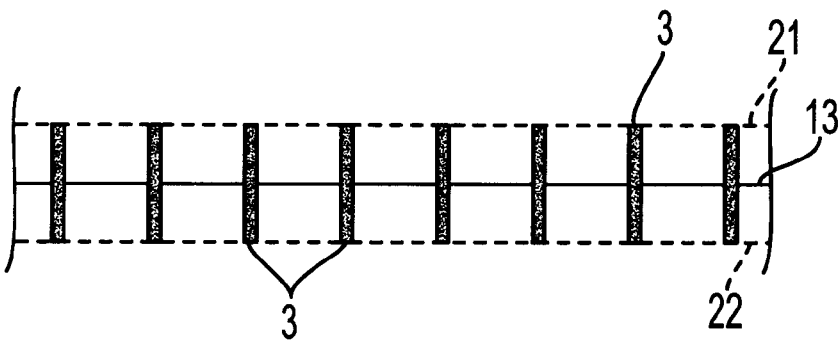
FIG. 21 is a schematic sectional view showing another arrangement of the elastic material sheet and the non-woven fabric of the present invention.

In an elastic sheet bonded on both sides by non-woven fabrics, assuming that the thickness of the elastic film is 50 $\mu$m, a single film sheet having a thickness of 50 $\mu$m or a two film sheet having a thickness of 25 $\mu$m can be used. Three different embodiments of the composite are illustrated in FIGS. 19 to 21:

(1) two elastic sheets (11, 12) each of which has a thickness of 25 $\mu$m are bonded to non-woven fabrics (21, 22) with bond sites (3), respectively, so as to provide two composite sheets laminated to each other, and the elastic sheets (11, 12) are bonded to each other by means of hot press (4) or the like (as shown in FIG. 19);

(2) two elastic sheets (11, 12) which have a thickness of 25 μm are bonded to non-woven fabrics (21,22), respectively, so as to provide two composite sheets laminated together. The elastic sheets (11, 12) are bonded to each other at bond sites (3) by means of hot press or the like (as shown in FIG. 20); and (3) two sheets of non-woven fabric (21, 22) are laminated to both sides of one elastic film sheet (13) having a thickness of 50 μm. The non-woven fabrics (21, 22) and the elastic film sheet (13) are bonded to each other at bond sites (3) (as shown in FIG. 21). An S—S curve of the composite structure of FIGS. 19 to 21 reveals an elevated elastic recovery property. In the case of FIG. 19, the bond sites (3) preferably do not overlap each other.

In a composite elastic material of the present invention, the morphology of the bond sites are important factors. In order to obtain an optimum S—S characteristics, the bond morphology is chosen so the characteristics of the non-woven fabric and the elastic sheet are optimized. The bond sites are preferably discontinuous in the desired elongating direction. That is, an unbonded site is positioned between bonded sites. The unbonded site facilitates adequate elongation of the composite sheet. An exemplary pattern of the bond sites is a set of dots, such as in the shape of a circle, a square or a polygon. The dots are preferably homogeneously distributed over the surface of the composite elastic material.

Two relatively thin sheets of non-woven, each of which is laminated to one side of an elastic sheet, are prepared. The non-woven/elastic laminate are joined to each other so that the elastic sheets face each other. The non-woven fabrics are laminated to the outer sides of the composite. When a polystyrene elastomer film such as SIS or S.E.B.S. is used as an elastic sheet, since the elastomer film is already adhesive, it is possible to manufacture a stable two-sided body merely by laminating the two films to each other. Consequently, productivity is improved, and the cost lowered. On the other hand, however, the self-adhesive property of this type of elastic film tends to cause adhesion when the surface of the film touches the surface of a roller, thereby potentially complicating the manufacturing process. Such complications can be avoided by adopting a process as shown in FIGS. 22 or 23.

Figure 22:
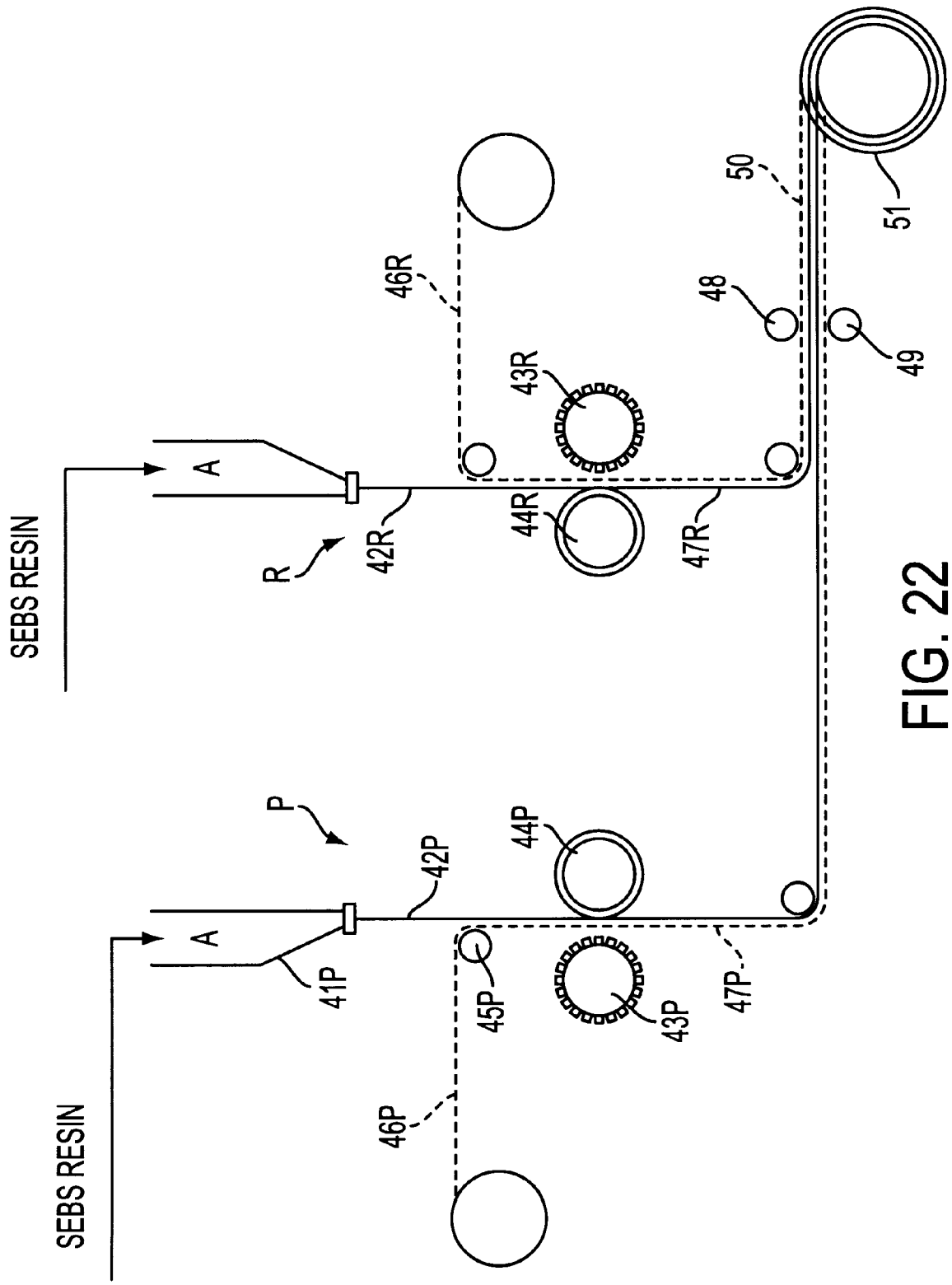
FIG. 22 schematically depicts a process for manufacturing the composite elastic material of the present invention.
Figure 23:
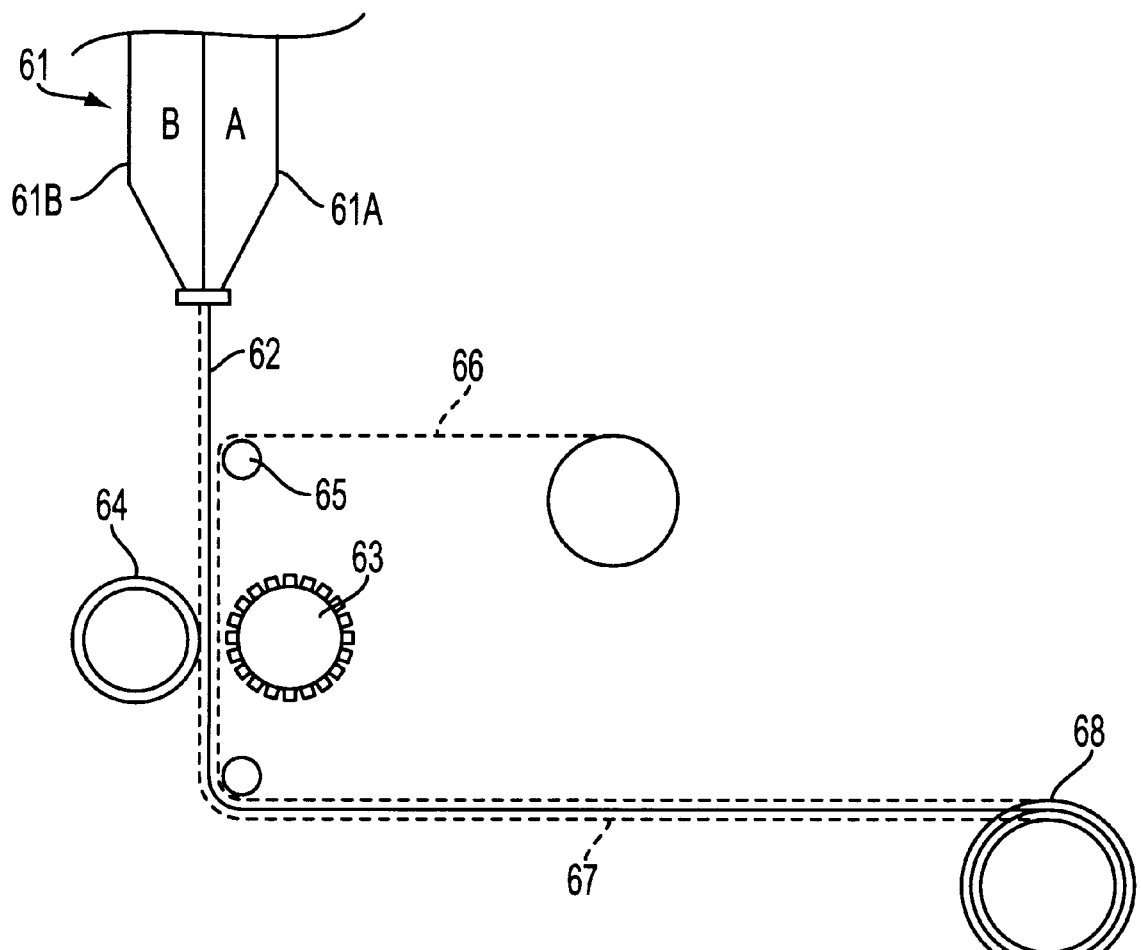
FIG. 23 is a schematic diagram showing another process for manufacturing the composite elastic material of the present invention.

In the process of FIG. 22, two parallel sections (P) and (R) for manufacturing the composite sheets are depicted. The first section (P) has an extruding machine (41P) which contains the raw material for forming an elastic sheet, such as an S.E.B.S. resin. Film (42P) which was extruded by the extruding machine (41P) is laminated to a spun-lace non-woven fabric (46P). Non-woven (46P) has been guided by a guide roller (45P) on the way to a nip which is positioned between a heated embossing roller (43P) and a chilling roller (44P). The first composite sheet (47P) is thus formed.

A second section (R) has substantially the same construction as that of the first section (P). A composite sheet (47R) is likewise formed in the second section (R). The composite sheet (47R) has the same structure as that of the first composite sheet (47P), except that non-woven fabric (46R) is laminated to a film (42R) so that the relative position of the non-woven fabric (46R) and the film (42R) is opposite to that of the second composite sheet (47P) and the film (42P). In the second section (R), similar elements are referenced with the same reference numerals.

Composite sheets (47P) and (47R) are then laminated to each other so that the films (42P) and (42R) face each other. Composite sheets (47P) and (47R) are guided to a nip between a pair of press rollers (48, 49). Each of the press rollers is chromed and is maintained at room temperature. Press rollers crimp two elastic sheets. Consequently, films (42P) and (42R) are bonded to each other by their own adhesive property. Finally, the four-layered composite elastic material (50) is wound by a product roller (51).

FIG. 23 shows an alternative manufacturing process for a three-layered composite. In FIG. 23, a film coextruding machine (61) has two chambers (61A, 61B). One chamber (61A) contains the raw material to form an elastic sheet, such as an S.E.B.S. resin (A). The other chamber (61B) contains an S.E.B.S./E.V.A. blended resin (B). The resins are extruded as a film from nozzles which are provided for each chamber, respectively. The two films touch one another while still soft to form a combined, two-layered coextruded film (62). The co-extruded film (62) passes through a-nip between a heated embossing roller (63) and a chilling roller (64). A spun lace non-woven fabric (66) is guided by a guide roller (65) and laminated to the exposed side of the S.E.B.S. resin film (62).

The heated embossing roller (63) has an embossing surface corresponding to a desired bond pattern. Consequently, the non-woven fabric (65) is bonded to the coextruded film (62) by the nip between the heated embossing roller (63) and the chilling roller (64) with a desired pattern. The resultant composite elastic sheet (67) is wound by a product roller (68).

The E.V.A. in the S.E.B.S./E.V.A. blended resin (B) advantageously provides an excellent elastic property. In view of the excellent elastic recovery property of the E.V.A., it is desirable that the thickness of the blended layer be as thin as possible.

Bond sites (3) in FIGS. 19–21 preferably extend in a band approximately perpendicular direction to the elongating direction of the elastic sheet and the non-woven fabric, preferably in a direction of 90°±10°. Such band-like bond sites bond the elastic sheet to the non-woven fabric with no space therebetween, or may include a plurality of bond sites oriented in a pre-determined direction.

Figure 24:
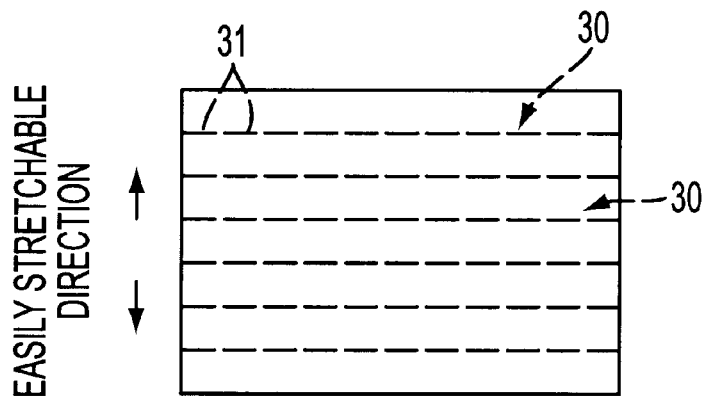
FIG. 24 is a plan view showing a pattern of discontinuous bond sites which are applied to the composite elastic material of the present invention.
Figure 25:
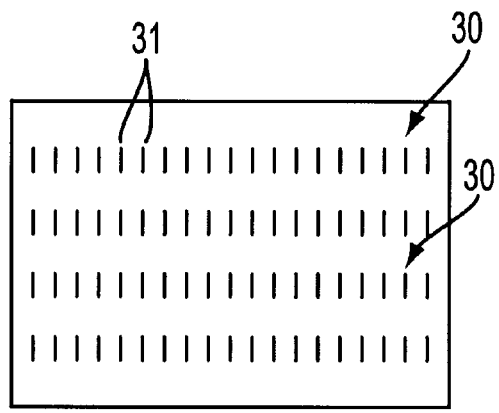
FIG. 25 is a plan view showing another pattern of discontinuous bond sites which are applied to the composite elastic material of the present invention.
Figure 26:
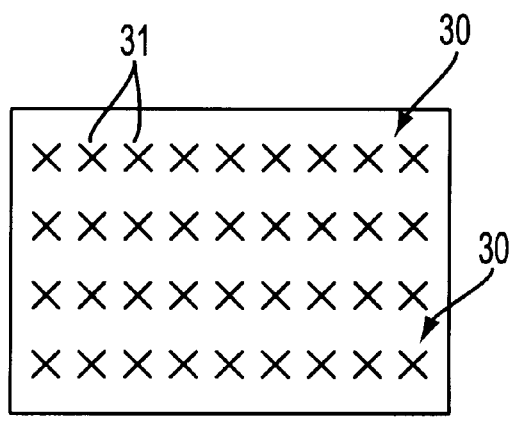
FIG. 26 is a plan view showing another pattern of discontinuous bond sites which are applied to the composite elastic material of the present invention.

Each of FIGS. 24 to 28 shows further preferred patterns of bond sites. In FIG. 24, a plurality of bond lines (30) are provided. Lines (30) are spaced in an approximately perpendicular direction to an elongatable direction of a composite elastic material and extend parallel to each other. In FIG. 25, a plurality of bond sites (31) are oriented in an approximately perpendicular direction to the machine direction.

Figure 27:
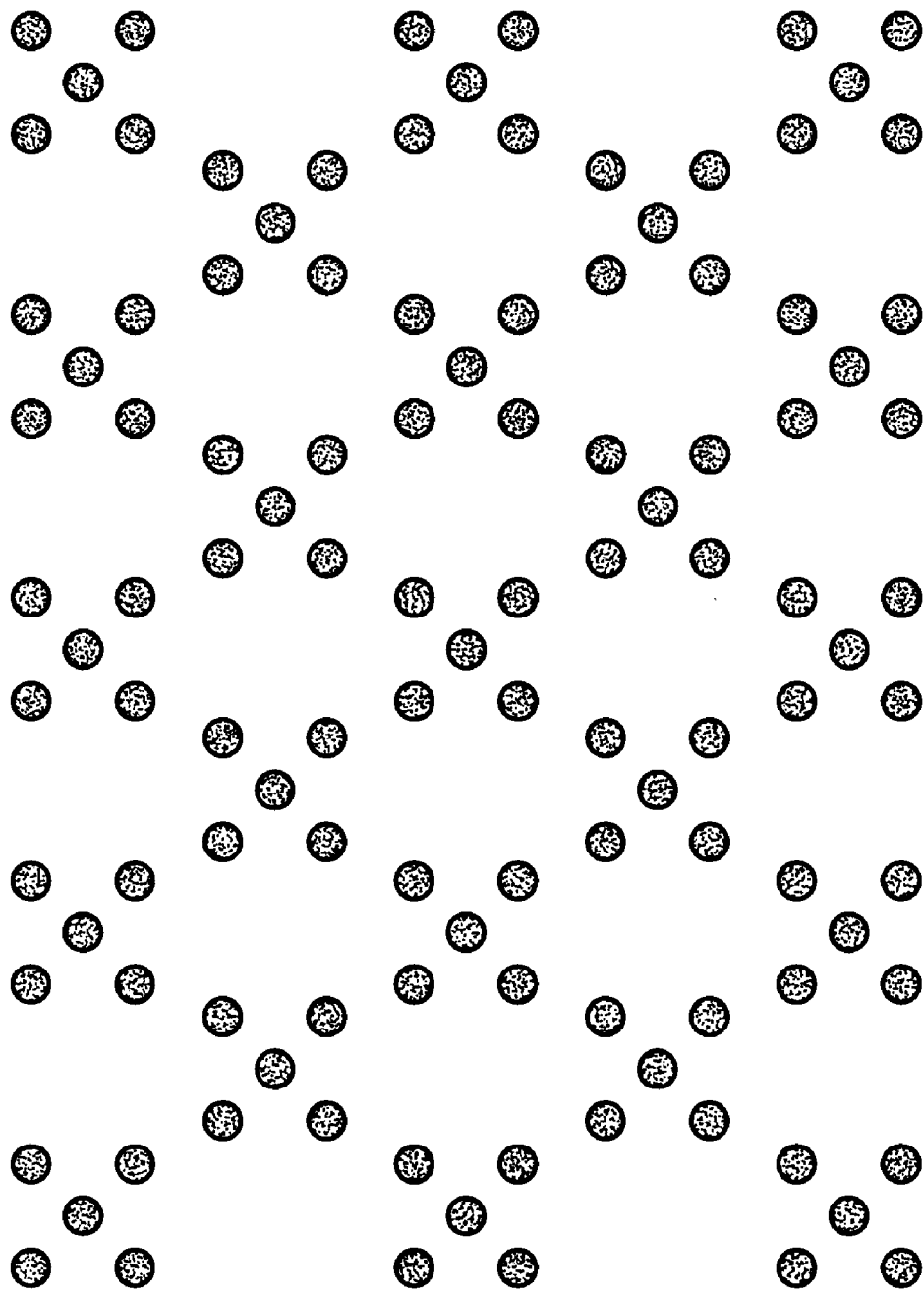
FIG. 27 is a plan view showing another pattern of discontinuous bond sites which are applied to the composite elastic material of the present invention.
Figure 28:
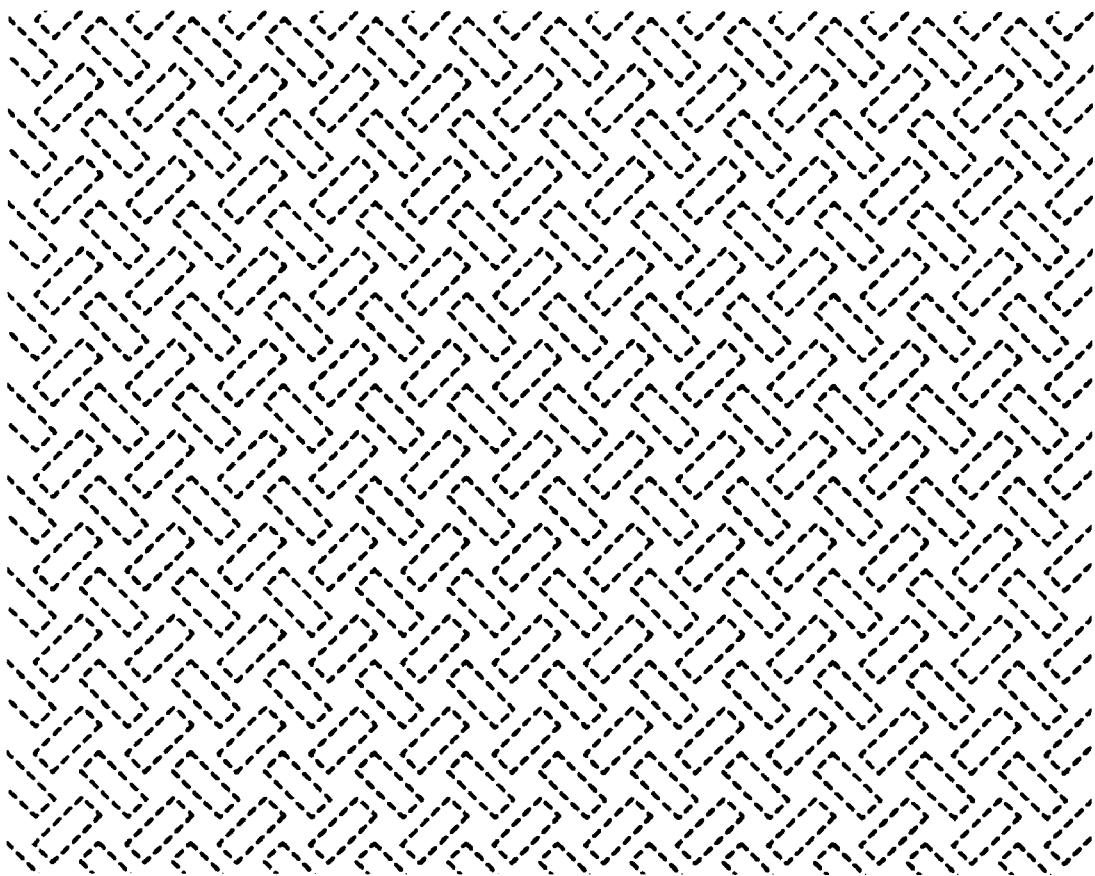
FIG. 28 is a plan view showing another pattern of discontinuous bond sites which are applied to the composite elastic material of the present invention.

In FIG. 27, each bond site (31) is shaped as an "x". The bond sites approximate a plurality of points of a lattice which comprises two sets of parallel lines crossing each other. Alternatively, the bond sites may be arranged as a pattern of alternately oriented rectangles at right angles to each other, having fine dots along the four sides of each of the rectangles, as shown in FIG. 28.

At the bond sites, the elongation properties of the non-woven and elastic sheet are substantially reduced so as to have substantially no elongating properties. Therefore, when the lines (30) of bond sites extend approximately perpendicular to the elongating direction of the composite as shown in FIG. 24, the elongating property changes little. When bond sites (30) are arranged to extend in parallel to the elongating direction, the elongating property is sharply lowered, even if the materials have a large elongating property in the parallel direction also. Therefore, a composite elastic material as shown in FIG. 25 has little elongation in the longitudinal direction of the lines (30).

On the other hand, with respect to the perpendicular direction of lines (30), the composite elastic material may be elongated without restriction until it reaches the elongation limit of the non-woven fabric. Then, when the tensile force of the composite elastic material is eased at the elongation limit, both the elastic sheet and the non-woven fabric recover to the original length thereof. However, if the composite elastic material is further elongated over the elongation limit of the non-woven fabric, the elastic recovery property of the composite elastic material is lost, and thereafter even if the tensile force is eased, the elastic sheet recovers to the original length, but the non-woven fabric is left in an elongated state. Consequently, when the composite elastic material recovers to the original length, the length of the non-woven fabric is longer than the elastic sheet, and the non-woven fabric becomes loosely attached to the elastic sheet between the lines of bond sites. Thus, after the non-woven fabric was elongated over its elastic limit, when the composite elastic material is again elongated, the composite elastic material may be re-elongated by a remarkably small force as compared to the tensile force which was necessary for the first elongation.

Figure 29:
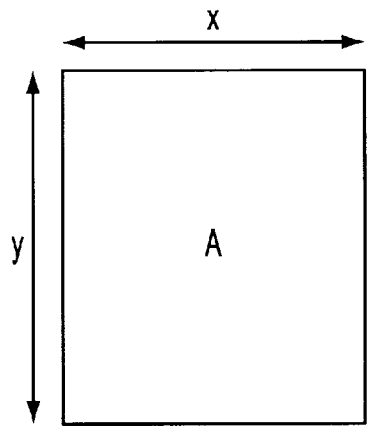
FIG. 29 is a plan view showing the direction of elongation of the composite elastic material of the present invention.
Figure 30:
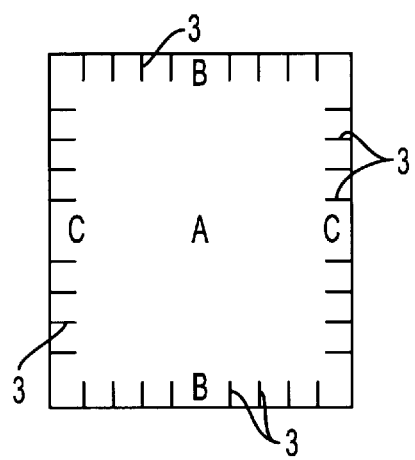
FIG. 30 is a plan view showing a configuration of discontinuous bond sites which are applied to the composite elastic material of the present invention.
Figure 31:
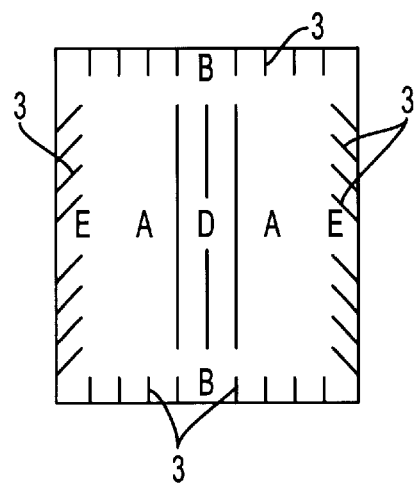
FIG. 31 is a plan view showing another configuration of discontinuous bond sites which are applied to the composite elastic material of the present invention.

FIG. 29 shows an approximately rectangular composite elastic material comprising a non-woven fabric and an elastic sheet having elongating properties in both the "x" and "y" directions. In FIG. 30, areas (B and C) extending along the four sides thereof are provided with linear bond sites (3) which extend in an approximately perpendicular direction to each of the sides. In area (A) of the composite elastic material, in which no linear bond sites (3) are provided, the composite elastic material may extend in any direction. In area (B), the composite has an elongating property only in the "x" direction. In area (C), the composite has an elongating property only in the "y" direction. Alternatively, as shown in FIG. 31, an area (D) extends in the "y" direction of the central portion of the composite. In areas (E), linear bond sites (3) are inclined at an angle of about 45 degrees to the sides, respectively. Areas (A) and (B) show a large elongating property in the "x" direction, while the area (E) shows an elongating property only in an inclining direction.

The direction of elongation may be specified by adding linear bond sites thereto as shown in FIGS. 30 or 31. Such selective elongation is useful when the resulting composite serves as a top sheet or back sheet of a diaper. Regions (A), (B), (D) and (E) may be made to have certain elastic properties typically found in the waist opening and the leg-hole of a diaper.

Figure 32:
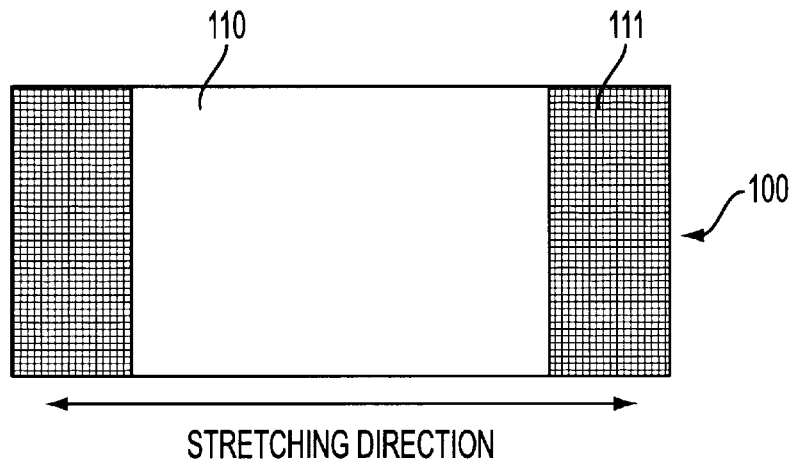
FIG. 32 is a plan view showing another configuration of discontinuous bond sites which are applied to the composite elastic material of the present invention.

FIG. 32 shows an composite elastic material (100) according to another preferred embodiment of the present invention. This composite elastic material has an elongating property only in one direction. The composite elastic material was subjected to a thermo-compression bonding treatment along the edges thereof (111). A first area (110), which is positioned in the center, has a large elongating property. The first area (110) is not subjected to the new thermo-compression bonding treatment. The second area (111) has very little elongating properties as a result of the thermo-compression bonding treatment. On the other hand, the bond of the second area (111) is strengthened by the treatment. Alternatively, in FIG. 33, three band-like areas (111) having a small elongating property are arranged with a prescribed space. In FIG. 34, areas (110) having large elongating properties are provided on both the sides of a band-like area (111) having a small elongating property.

Each of the elastic sheets and the non-woven fabrics in the foregoing embodiments is preferably formed from a material which is easily melted by heating. Non-woven fabrics such as polyester and polyethylene, and having a conjugated resin web which has a sheath of polyethylene and a core of polyester, may be used. The elastic sheet is preferably a film comprising S.E.B.S. (styrene-ethylene-butadiene-styrene block copolymer). This composite elastic material is easily joined by ultrasonic sealing and is readily adaptable to high-speed manufacturing processes.

Figure 35:
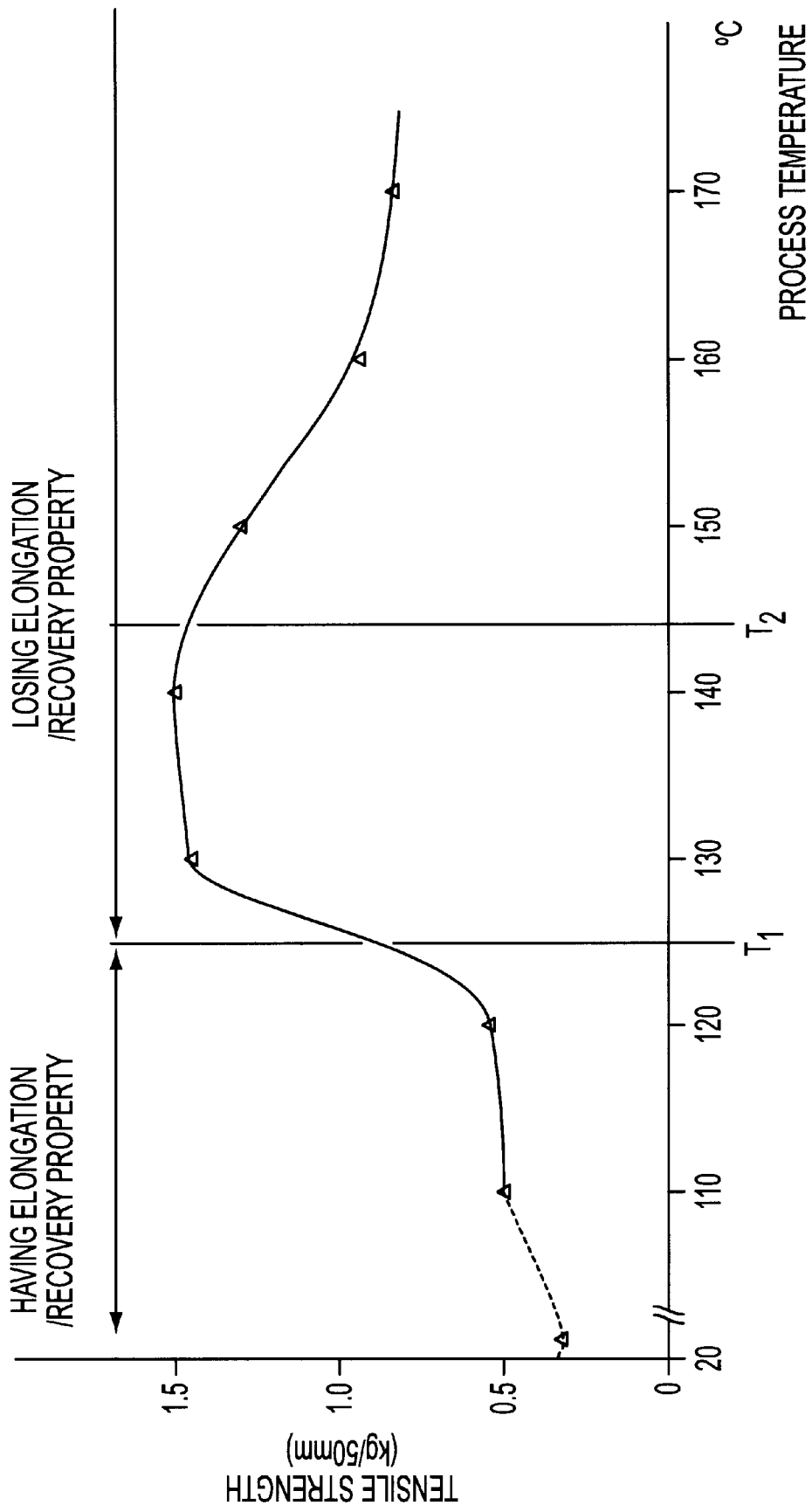
FIG. 35 is a graph showing the results obtained from the measurement of the relationship between process temperature and tensile strength of the composite elastic material of the present invention.

FIG. 35 is a graph which shows the relationship between temperature and tensile strength, which were measured while the composite elastic material was thermo-compression bonded. The composite elastic material was formed by laminating an elastic sheet of SIS film to a non-woven fabric of water entangled PET fiber. The resulting laminate was partially thermo-compression bonded. "T1" and "T2" represent the melting point of SIS, and the melting point of PET, respectively. As can be seen in FIG. 35, at a temperature of T1 or less, hardly any thermo-compression bonding between the elastic sheet and the non-woven fabric is realized. While an acceptable elongation recovery property is observed, the tensile strength is low. When the thermo-compression bonding is carried out between T1 and T2, at least part of the elastic sheet is melted and bonded to the non-woven fabric. As a result, the elongation recovery property is lost, but the tensile strength sharply elevates. When the thermo-compression bonding is carried out above T2, both the elastic sheet and the non-woven fabric are melted, and the composite elastic material has little elongating properties in any direction.

Figure 33:
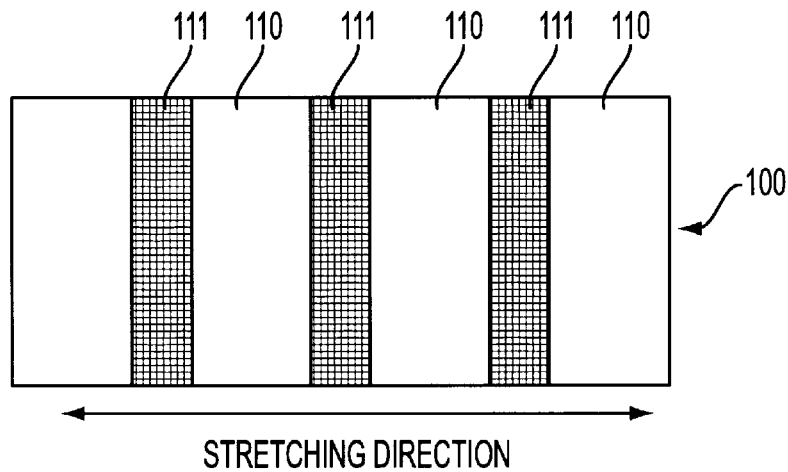
FIG. 33 is a plan view showing another configuration of discontinuous bond sites which are applied to the composite elastic material of the present invention.
Figure 34:
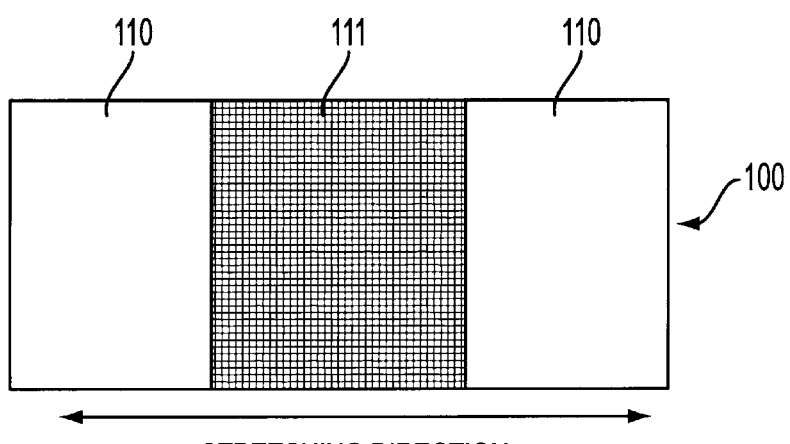
FIG. 34 is a plan view showing another configuration of discontinuous bond sites which are applied to the composite elastic material of the present invention.

In FIGS. 32 to 34, a composite elastic material may be formed by bonding at different temperatures and locations along the length thereof. By partially subjecting the elastic sheet and the non-woven fabric to a thermo-compression bonding at a temperature between T1 and T2 for the area (110), and by wholly subjecting them to a thermo-compression bonding at a temperature T1 or more for the area (111), the elongation characteristics of the composite may be appropriately controlled. Area (110) has a large elongation property but its elongation is restricted or controlled by the small elongation property of the area (111). Thus, the elongation property in a prescribed elongating direction may be made large, while an elongation property in another direction may be very small. If the thermo-compression bonding occurs at a temperature of T2 or more, the parts become fragile.

The composite elastic material as specified has areas of large and small elongation and can be applied to various products. As one example, the composite elastic material in which areas (111) having small elongation properties are formed on both the sides of an area (110) having a large elongation property as shown in FIG. 32 can be applied to a tape-less type (pants type) of absorbent product.

Figure 36:
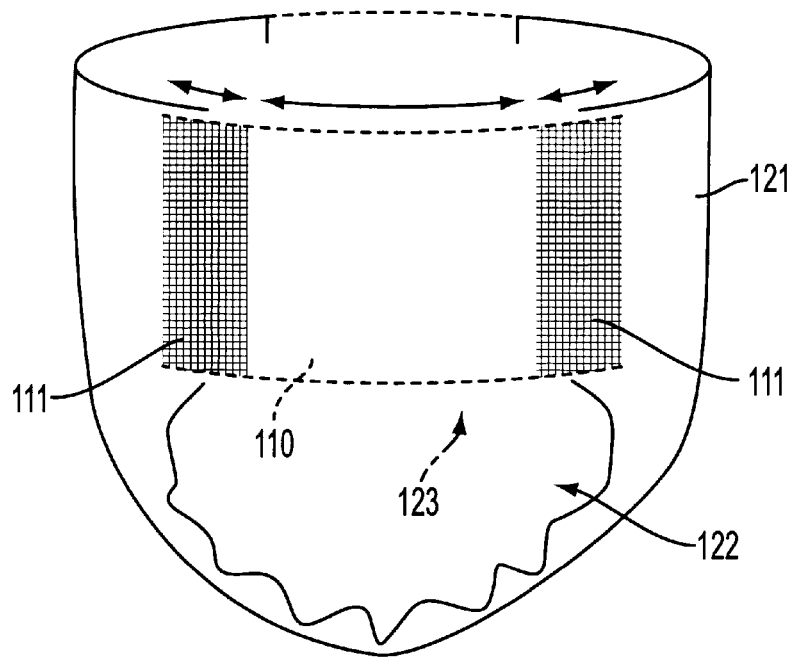
FIG. 36 is a perspective view showing an absorbent product in which the composite elastic material having the S—S characteristic curves shown in FIG. 13 is used as a side panel.

An absorbent product as shown in FIG. 36, i.e., a tape-less diaper, comprises a main body (121) bent into an approximate U-shape and two leg holes (122). The opposite side-hems are connected to each other with a side panel (123) comprising a composite elastic material (100) as shown in FIG. 32. The main body (121) has an absorbent housed between a liquid pervious top sheet and a liquid impervious back sheet. Composite elastic material (100) is bonded to the main body (121) at (111) which is positioned on both ends thereof. Area (111) has a small elongation property. Unbonded area (110) has a large elongation property. The composite elastic material (100) thus functions as the side panel of the garment and is bonded to the main body (121) at area (111) which has a relatively large bond strength at both the ends thereof.

Figure 37:
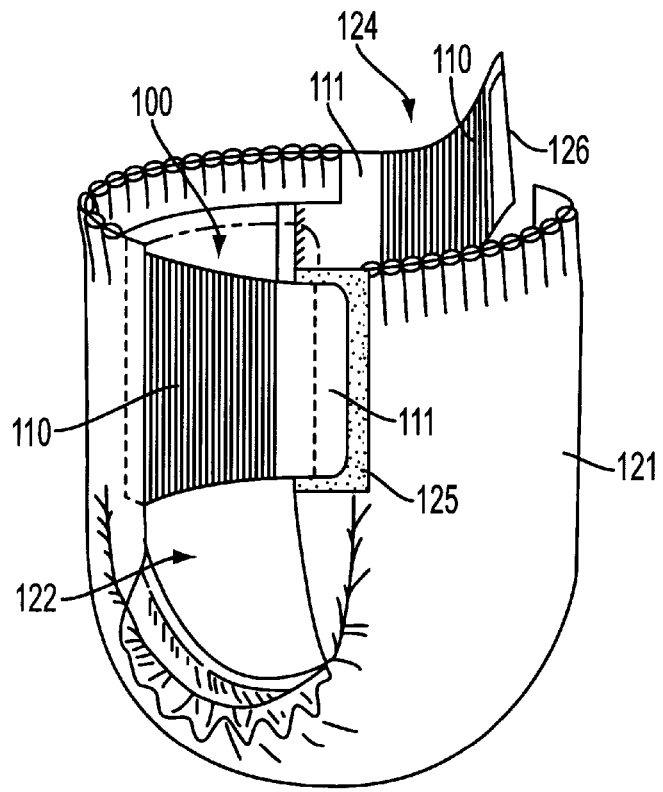
FIG. 37 is a perspective view showing an absorbent product in which the composite elastic material having the S—S characteristic curves shown in FIG. 13 is used as a side panel.

FIG. 37 illustrates a diaper having a side band (124) comprising a composite elastic material (100) as shown in FIG. 33. Side band (124) is bonded to the main body (121)

at an area (111) having a small elongation property. Fastener (126) e.g. hook and loop fastener, is affixed at an area (111) having a small elongation property. Fastener (126) may be removably attached to bond area (125). The diaper can be easily removed by unfastening fastener (126). The waist portion of the diaper can be fitted to the waist of a wearer by virtue of the large elongation property of area (110).

The composite elastic material (100) may be predrawn before being applied to the main body (121) of the diaper. Alternatively, composite elastic material (100) may be predrawn after being applied to the main body (121) by using a predrawing machine incorporated in the manufacturing line.

The foregoing examples are applicable to stretching mainly in the CD. However, it is also possible to stretch the composite in the MD. Finally, the composite elastic material may have elastic properties in both the CD and MD.

Figure 40:
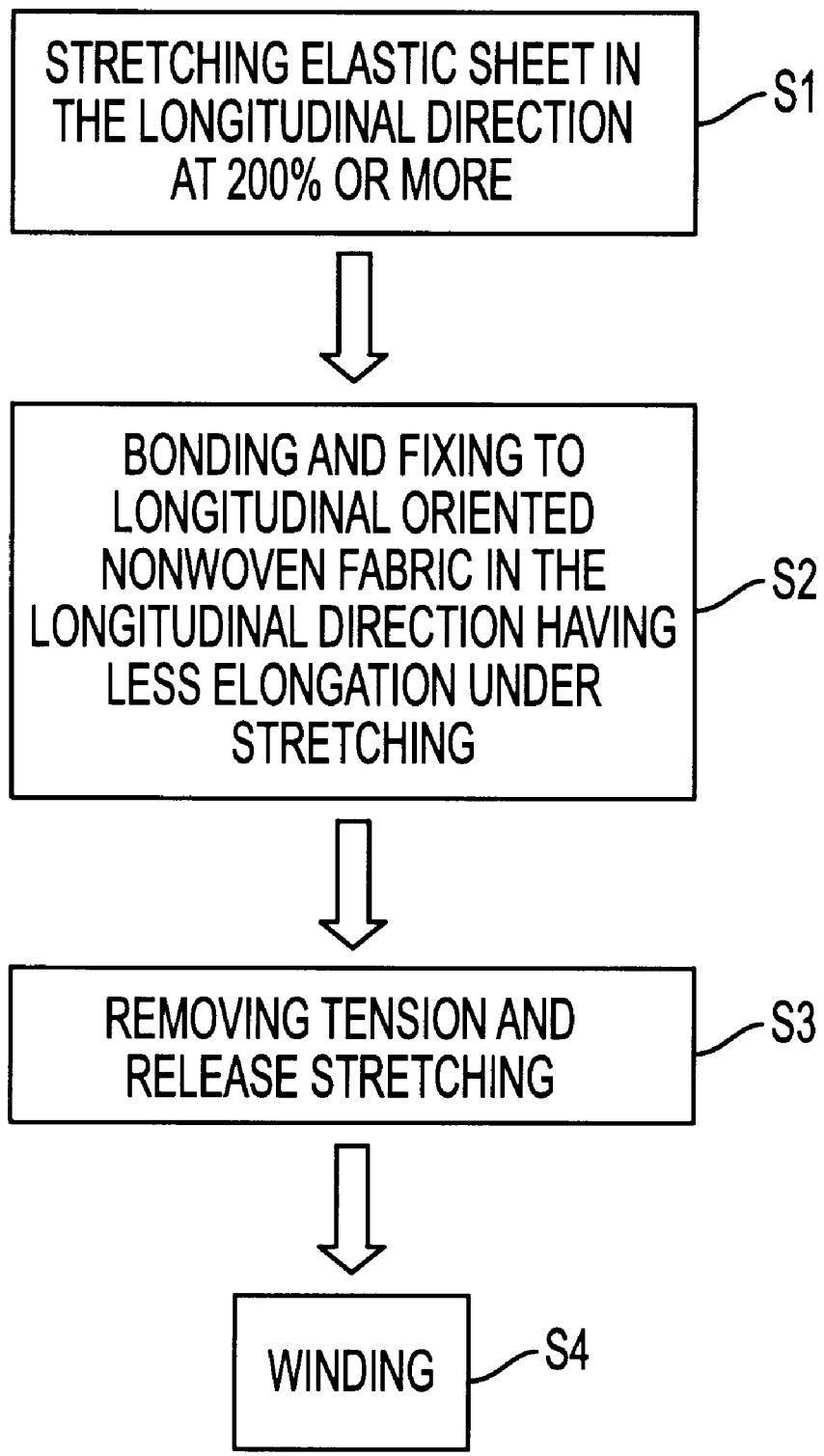
FIG. 40 is a schematic diagram showing another process for manufacturing a composite elastic material having elastic properties in both warp and weft directions according to the present invention.

FIG. 40 shows a process for manufacturing a composite elastic material having an elastic property in both the CD and MD by combining an S.B.L. with a non-woven fabric readily stretchable in the CD. In this process, an elastic sheet is elongated by 200% or more in the machine direction (Step S1). Next, a non-woven fabric having a small elongation property in a machine direction is elongated within the elastic limit thereof and laminated to the elastic sheet, so that the elastic sheet and the non-woven fabric are joined to each other (Step S2). Then, the elongation of the joined sheet is eased (Step S3). Finally, the composite elastic material is wound on a storage roll (Step S4).

Examples of the present invention will be explained as follows.

EXAMPLE 1
Manufacture of Nonwoven Fabric Having Elongation Properties 50 parts of a polyester fiber (1.5 d×35 mm) and 50 parts of a thermoplastic conjugated fiber ("Melty") (2 d×51 mm) of a polyester sheath-core type were mixed so as to prepare a card web having a basis weight of 30 g/m$^2$ by using a roller card. The ratio of MD/CD of the web was approximately 3.5. The web was introduced onto a net conveyer which had two types of high pressure water-jets. The web was then subjected to a water entanglement at a speed of about 30 m/min. on a net which had a dewatering zone. The conditions of the water entanglement were as follows:

First Treating Zone
  Number of Nozzle Lines 2 sets
  Nozzle Diameter: 0.15 mm
    Spacing: 0.6 mm
  Water Pressure 50 kg/cm$^2$
Second Treating Zone
  Number of Nozzle Lines 2 sets
  Nozzle Diameter: 0.20 mm
    Spacing: 1.00 mm
  Water Pressure 70 kg/cm$^2$ The web after water entangling was dewatered, and introduced into a hot-air dryer. The maximum temperature was about 1300° C. After exiting the dryer, the web was drawn by approximately 30% in a heated state, and then cold wound.

The non-woven fabric obtained thereby had a basis weight of 22 g/m$^2$ and a directional difference of MD/CD=8. A elongation percentage after breaking in the CD was about 280%.

Manufacture of Elastic Body Sheet 65 parts of S.E.B.S. resin (trade name "SEPTON #8007" made by KURARAY, CO., LTD.), 35 parts of E.V.A. resin (trade name "EVA FLEX P-1907" made by Mitsui DuPont Ltd.), and 0.1 parts of an oxidation inhibitor (trade name "RUGANOX 1010" made by Mitsui DuPont Ltd.) were added and mixed, and melted-pelletized to prepare a compound. The MFR (g/10 min.) of the compound was 7.8 at a temperature of 2300° C. and a pressure of 2.16 kg.

Forming and Winding of Elastic Film

A film having a thickness of 20 μm was formed by using a die-extruding machine. Since this film is very adhesive, if it is wound as it is, it becomes difficult to separate the film. Therefore, the film was laminated to the non-woven fabric before winding.

Manufacture of Jointed Body in Which Nonwoven Fabric is Jointed at One Side

The non-woven fabric and elastic film are temporarily jointed by virtue of the self adhesion of the film. This sheet is then laid onto a 40-mesh plastic net. The three layers are then passed through a pressure apparatus comprising a heated grid roller/flat roller. Accordingly, the elastic film and the non-woven fabric are partially welded. The heat was applied to the non-woven fabric side of the laminate. The specifics of the heating-pressure apparatus is as follows:

Upper Roller (Grid Roller)
  Height of Thread: 1.0 mm
  Width of Top: 1.5 mm
  Grid Spacing: 3.0 mm
  Inner Heat Medium Heating
  Process Temperature: 1300° C.
  Surface Treatment: Chrome Plating
Lower Roller (Flat Roller)
  Surface Treatment: Chrome Plating
  Process Temperature: 1300° C.
Pressure: 40 kg/cm$^2$
Winding Speed: 20 m/min.

The joint pattern of the composite elastic material had a pattern as shown in FIG. 25.

Manufacture of Jointed Body in Which Nonwoven Fabrics Are Jointed at Both Sides

Two composite sheets were bonded to each other so that the sides with the film face one another and the non-woven fabrics face the outer sides thereof. Since the self adhesion property between the films is very large, the films are easily joined to each other by laminating and thermo-compressing the films. When the two sheets were passed through two flat rollers which were heated to 800° C., the composite elastic material as shown in FIG. 19 was obtained.

Determination of S—S Curve of Composite Elastic Body

With reference to FIG. 2, an S—S curve which results in a complete breaking of the composite elastic material was determined. A stress-lowering point occurs at approximately 230% when the sections of the non-woven fabric breaks. Another stress-lowering occurs at approximately 420% when the film breaks.

Determination of S—S Curve of Drawn Article

Three composite samples of the preferred embodiments were prepared, each of which were predrawn by 75%, 100% and 150%, respectively. An S—S curve of each sample, which results in complete breaking, were determined. The results are shown in FIGS. 3 to 5. First stress-lowering point and a second stress-lowering point are clearly observed and may be used as warning signs that breakage is imminent. Some of the strain is removed by drawing, thereby providing a homogeneous structure which elongates to a greater degree than a non-pre-drawn article.

The drawing reduces the elongating stress. This is an important point of the present invention, and is believed to be based on the elongation activation. A composite elastic material which was drawn has four areas of elongation properties, as shown in FIG. 6.

EXAMPLE 2

Manufacture of Nonwoven Fabric Having Elongation Properties 50 parts of a polyester fiber (⅕ d×35 mm) and 50 parts of a polyester fiber (2 d×51 mm) were mixed to prepare a parallel card web of 25 g/m² by using a roller card.

The difference between the MD and CD strength of the web was on the order of MD/CD=7. This web was introduced onto a multiple aperture suction cylinder which was provided with three nozzles and a dewatering zone. After water saturation, deration and dewater, the web was passed through the nozzles at a velocity of 30 m/min. for water entanglement:

First Nozzle: 0.12 mm×0.4 mm Spacing
    Water Pressure 30 kg/cm²
Second Nozzle: 0.12 mm×0.4 mm Spacing
    Water Pressure 50 kg/cm²
Third Nozzle: 0.20 mm×1.5 mm Spacing
    Water Pressure 60 kg/cm²

The web was dried and heated to obtain a non-woven fabric. An S—S curve of the non-woven fabric at a first stress-lowering point in the CD is illustrated ad Curve A in FIG. 38.

Preparation of Elastic Body Sheet

A blended resin comprising a polyolefin elastomer of EMA/EPDM was extruded to form an elastic film having a thickness of 25 μm. An S—S curve in the CD of the elastic sheet is illustrated as Curve B in FIG. 38.

One Side Jointed Body

The above-mentioned non-woven fabric and elastic sheet were laminated to each other, and placed on a 60-mesh PFT net so that the elastic sheet is on the side of the PFT net, and then thermo-compressed at a linear load of 10 kg/cm with an embossed heated roller at 1100° C. The heated roller is applied to the non-woven fabric, while a flat roller contacts the net.

Figure 38:
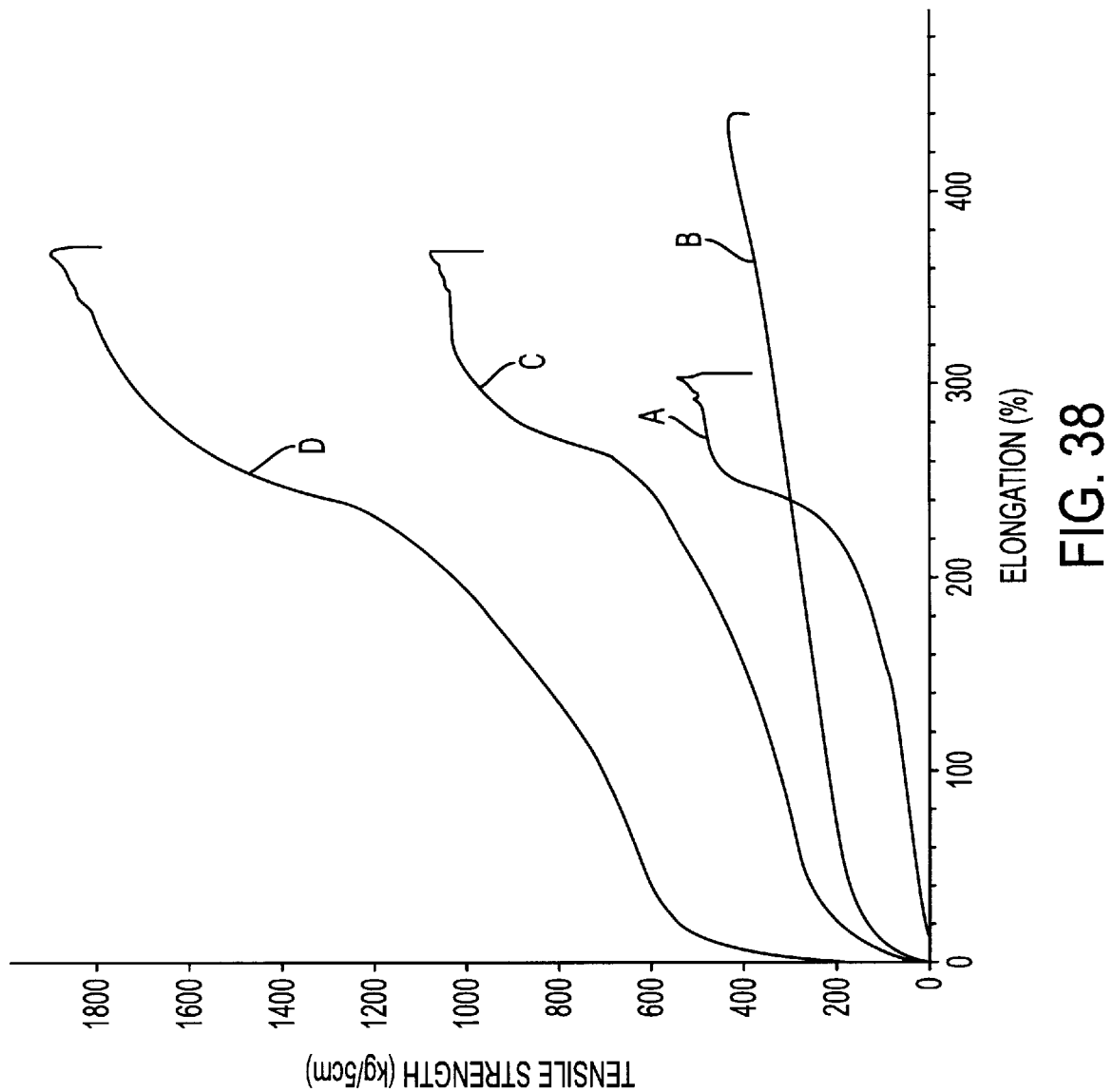
FIG. 38 depicts S—S curves of a composite elastic material, an elastic material sheet and a non-woven fabric, respectively, in the CD.

An S—S curve at a first stress-lowering point in the CD of the composite elastic material is illustrated in Curve C in FIG. 38.

The composite elastic material was elongated three times to 150% as shown in FIG. 7. The composite elastic material had a recovery percentage of 75%.

Both Sides Jointed Body

Two sheets of the above-mentioned one-sided jointed body were laminated to each other so that the film sides can face each other. The laminate was passed through a heated roller having a flat surface at a temperature of 800° C. with a linear load of 20 kg/cm at a velocity of 10 m/min. The positions of joint points were shifted so that the inside joints do not overlap the outside joints. An S—S curve with a first stress-lowering point in the CD is illustrated as Curve D in FIG. 38.

The composite elastic material was elongated three times to 150% as shown in FIG. 8. The composite elastic material had a recovery percentage of 75%.

EXAMPLE 3

One Side Jointed Body of S.E.B.S. Film and Nonwoven Fabric

A composition was extruded to prepare an elastic film having a thickness of 25 μm. The composition comprised a resin blended with 75 parts S.E.B.S. and 25 parts E.V.A. The film easily adheres to itself merely by crimping it at room temperature. A rubber hot melt adhesive was sprayed in a very small amount (approximately 0.4 g/m²) on one side of the film, and jointed to a non-woven fabric which is similar to the one used in Example 1, by crimping all over the surface.

Both Sides Jointed Body

Two sheets of composite material, each having a non-woven fabric jointed to one side of the above-mentioned S.E.B.S. film are laminated to each other along their respective adhesive surfaces. The laminate was then passed between a pair of flat rollers at a linear load of about 20 kg/cm² at a temperature of about 400° C. The one-side jointed body and the two-sided jointed body have an elongation recovering property which is similar to the one in Example 1, respectively.

EXAMPLE 4

Preparation of Nonwoven Fabric as Raw Material

A spun-bond non-woven fabric (trade name "ELVES" made by UNITIKA, LTD.) with a conjugated fiber has a polyester core as a skeleton component(B) and a polyester sheath as a jointing component(A), and has a width of 1 m and a weight of 25 g/m². This non-woven fabric is manufactured by a spun-bond process. Spot bond-points are distributed along the web with a predetermined density. The percentage of the distributed spot bond-points was approximately 8% as a ratio thereof to the whole area. The PET skeleton component (B) had a plasticizing temperature of about 1900° C., and a stable temperature of about 1000° C. to about 1300° C.

Tensile Strength
    Machine Direction: 12.5 kgf/5 cm
    Cross Direction: 4.5 kgf/5 cm
    Ratio of Machine/Cross: 2.8
Elongation Percentage after Fracture
    Machine Direction: 60%
    Cross Direction: 60%
    Ratio of Machine/Cross: 1

The above-mentioned spun-bond non-woven fabric was introduced into a pressure steaming machine which is provided with a clip tenter at a speed of about 10 m/min., and heated to about 1050° C. to 1150° C. in the steaming machine while being expanded about 1.5 times its original width. The non-woven fabric ejected from the steaming machine was dried at room temperature and wound. Some water was left in the widened non-woven fabric. The basis weight thereof was about 18 g/m². Then, the widened non-woven fabric was passed through a multiple aperture cylinder which included a steam generator so as to draw it to about 2.2 times the natural length thereof in the machine direction (MD). Then, the fabric was dried in hot air at a temperature of about 600° C. and wound. The basis weight thereof was about 22 g/m².

The resultant easily stretchable non-woven fabric had mesh apertures, was soft, and was readily stretchable in the cross direction.

The physical properties were as follows:
Tensile Strength
    Machine Direction: 8.7 kgf/5 cm
    Cross Direction: 1.5 kgf/5 cm
    Ratio of Machine/Cross: 5.8
Elongation Percentage after Fracture
    Machine Direction: 30%
Cross Direction: 280%
Ratio of Machine/Cross: 9.3

As compared with the non-woven fabric of the raw material, the drawn non-woven fabric has increased elongation percentages in the cross direction (i.e., perpendicular to the drawing direction).

Manufacture of Elastic Body Compound 45 parts of S.E.P.S. (trade name "SEPTON #4033" made by KURARAY CO., LTD.), 30 parts of LDPE (trade name "LM31" made by UNITIKA, LTD.) and 25 parts of a processed oil (trade name "DIANA PW-380" made by UNITIKA, LTD.) were mixed to prepare a pelletized compound. An MFR (g/10 min.) of the compound was 14 at a temperature under a pressure of 2.1 kg.

Formation of Elastic Film and Jointing of Nonwoven Fabric Having Elongation Property By using the above-mentioned compound, a film having a thickness of 30 $\mu$m was obtained through a die forming machine. Before cooling, the film was laminated to the above-mentioned spun-bond, passed through a pair of flat press rollers, and thereafter passed through a pair of heat embossed rollers. The heat embossing was applied to the non-woven fabric.

Upper Roller (Embossed Projecting Roller)
Height of Thread: 0.8 mm
Pattern: Pattern as Shown in FIG. 27
Grid Spacing: 3.0 mm
Inner Heat Medium Heating
Process Temperature: 1200° C.
Surface Treatment: Chrome Plating
Lower Roller (Flat Roller)
Surface Treatment: Chrome Plating
Process Temperature: Room Temperature
Pressure: 30 kg/cm$^2$ A composite elastic material comprising a film and a non-woven fabric having an elongation property was thus obtained. The resultant composite elastic material showed excellent elasticity properties similar to each of the above-mentioned Examples.

EXAMPLE 5

A non-bonded web of PET spun-bond having a basis weight of about 10 g/m$^2$ was prepared as a skeleton component (B), and laminated to a melt-blown web having PE of a basis weight of about 7 g/m$^2$. The web was mesh bonded to prepare a double-layer non-woven fabric of about 24 g/m as shown in FIG. 16. This double-layer non-woven fabric was drawn to about 1.8 times the natural length thereof, while being heated by multistage rollers. Heat was provided with infrared lamps in the upper and the lower sides thereof at a temperature of about 1200° C.

The physical properties of the fabric were as follows:
Tensile Strength
Machine Direction: 9.5 kgf/5 cm
Cross Direction: 0.85 kgf/5 cm
Ratio of Machine/Cross: 11.0
Elongation Percentage after Fracture
Machine Direction: 30%
Cross Direction: 830%
Ratio of Machine/Cross: 6

The non-woven fabrics were laminated onto both sides of an elastomer film and laminated to a 40-mesh plastic net, and then passed between a pair of flat rollers under a pressure of about 2 kg/cm$^2$ to obtain a composite elastic material with a point-joint. The elastomer film has S.E.B.S. as the main component thereof. The elastomer film was 40 $\mu$m and is made by U.S.A. KUROPEI LTD.

The composite elastic material exhibits excellent elasticity properties. It has a first breaking point based on breaking of the non-woven fabrics and a second breaking point based on breaking of the elastic material. The elastic properties were as follows:
Residual Strain: 15%
First Stage Elongation after Fracture: 185%
Second Stage Elongation after Fracture: 385%

EXAMPLE 6

Burst fiber webs of polypropylene were laminated to both sides of a widened web of polyester tows having a basis weight of about 30 g/m$^2$ to obtain a non-woven fabric (trade name "UNICEL" made by TEIJIN LTD.). The structure is as shown in FIG. 17, and the physical properties of the non-woven were as follows:
Tensile Strength
Machine Direction: 6.3 kgf/5 cm
Cross Direction: 6.5 kgf/5 cm
Ratio of Machine/Cross: 1.0
Elongation Percentage after Fracture
Machine Direction: 80%
Cross Direction: 60%
Ratio of Machine/Cross: 0.8
Heating Conditions The above-mentioned non-woven fabric has a width of about 1 m and was treated by a thermal pretreatment unit shown in FIG. 39. The unit comprises belt conveyor (71), a drawing machine (72), a dryer (73) and a winder (74). The above-mentioned non-woven fabric was first fed from conveyor (71) to the drawing machine (72) which comprises two press rollers (75, 76) and nine rollers (77 to 85) which are arranged in two stages. Roller (77) faces the press roller (75), and roller (85) faces press roller (76). Rollers (79, 80, 83 and 84) are positioned in hot-water bath (86). Steam is introduced in the hot-water bath (86) which is maintained near the boiling point of water.

The non-woven fabric ejected from the conveyer (71) is passed between rollers (75) and (77), and passed over the roller (78) which acts as a widening roller. Then, the fabric is passed over rollers (79–84), and finally passed between press roller (76) and roller (85). By passing over each roller, the non-woven fabric is drawn in stages while heated. The drawn non-woven fabric is introduced into hot air dryer (73), and then wound by winder (74).

In this Example, the non-woven fabric was drawn to about 2.0 times its natural length at a speed of about 20 m/min., and dried in hot air at a temperature of about 700° C. in the dryer (73). The resultant non-woven fabric is soft and has a large stretchable property in the weft direction. The basis weight is about 20 kg/m$^2$. The resultant non-woven fabric has a lacelike appearance, and is readily stretchable in a weft direction. The physical properties of the non-woven fabric are as follows:
Tensile Strength
Machine Direction: 4.0 kgf/5 cm
Cross Direction: 1.1 kgf/5 cm
Ratio of Machine/Cross: 3.6
Elongation Percentage after Fracture
Machine Direction: 42%
Cross Direction: 258%
Ratio of Machine/Cross: 6.1

The elongation percentage in the cross direction is substantially increased as compared with the raw material before drawing.

The non-woven fabrics were laminated to both sides of a netty S.E.B.S. elastic material (trade name "NETRON" made by Mitsui Petrochemical Industries, Ltd) having a basis weight of about 110 g/cm², and wholly thermo-jointed with spots. The resultant non-woven fabrics exhibited improved elasticity properties, and had a first breaking point based on breaking of the non-woven fabrics, and a second breaking point based on the breaking of the elastic material. A first-step elongation percentage after breaking was about 320%, and a second-step elongation percentage after breaking was about 440%.

EXAMPLE 7

Preparation of Easily Extensible Nonwoven Fabric in Cross Direction

Figure 39:
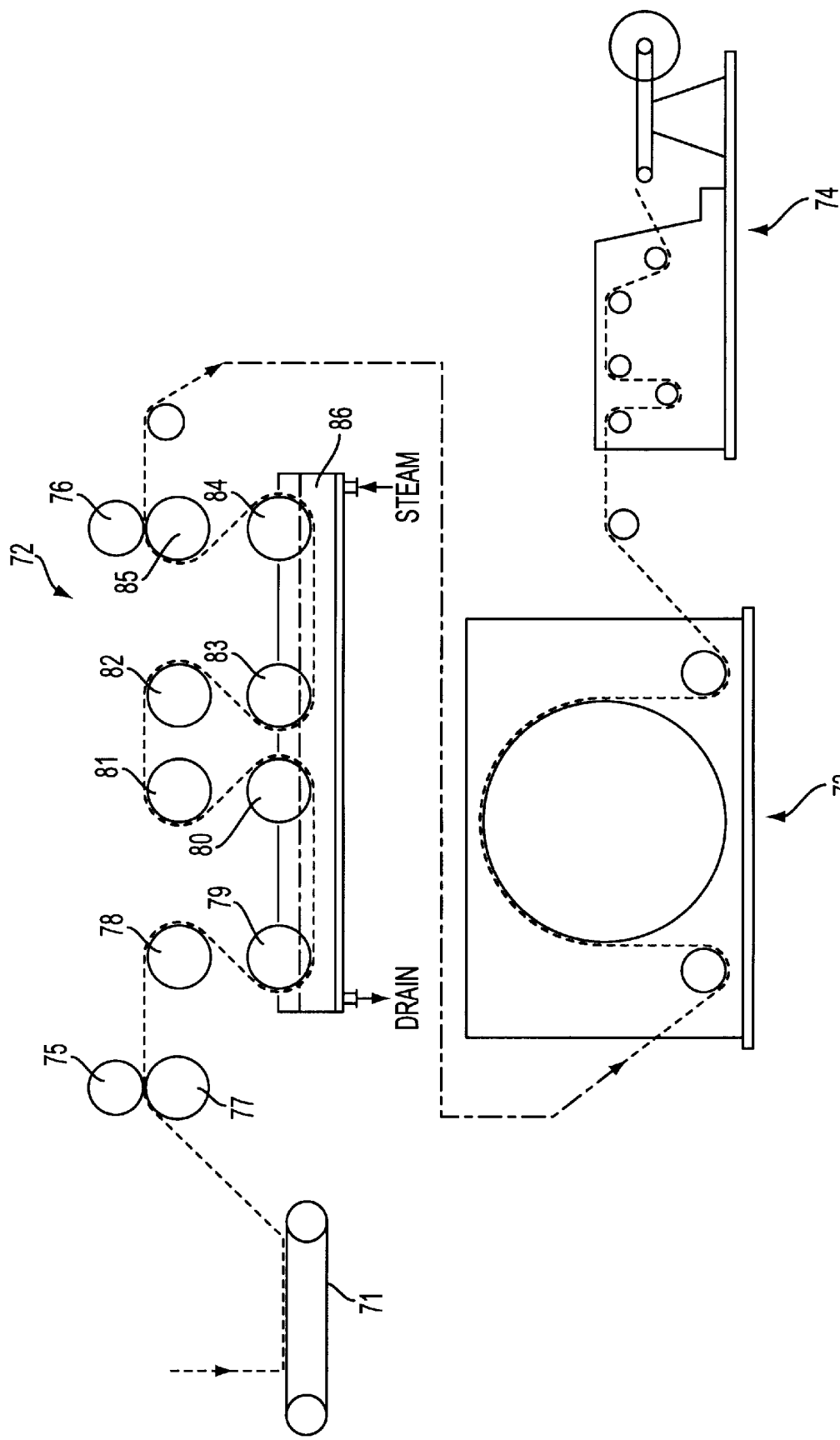
FIG. 39 shows the process for drawing a non-woven fabric which is used for a composite elastic material of the present invention.

A spun-bond non-woven fabric (trade name "ELVES" made by UNITIKA, LTD.) having a basis weight of about 25 g/m² was drawn to about two times its length in the machine direction according to the process of FIG. 39. The resulting non-woven fabric had a basis weight of about 18 g/m². The spun-bond non-woven fabric included a conjugated fiber which has a polyester core and a polyethylene sheath at a 50/50 ratio. The resulting fabric had the following properties:

Tensile Strength
  Machine Direction: 6.8 kgf/5 cm
  Cross Direction: 1.4 kgf/5 cm
  Ratio of Machine/Cross: 5.0
Elongation Percentage after Fracture
  Machine Direction: 40%
  Cross Direction: 220%
  Ratio of Machine/Cross: 5.5
Preparation of Elastic Sheet A resin (Ra) having S.E.B.S. as a main component and a blended resin (Rb) of S.E.B.S. of 60%/E.V.A. of 40% were used to prepare a coextruded film according to a process as shown in FIG. 23. The resultant film had a thickness of 50 μm (Ra layer: 35 μm, Rb layer: 15 μm). The physical properties of the film were determined, and the following values were obtained:

TABLE 1

Performance of Applied Resins

|    | Specific Gravity | Hardness | MFR (g/10 mm) | 300% Modulus (kg/cm²) | Tensile Strength (kg/cm²) | Elongation (%) |
| --- | --- | --- | --- | --- | --- | --- |
| Ra | 0.95 | 65 | 8 | 25 | 237 | 750 |
| Rb | 0.88 | 68 | 9.7 | 26 | 120 | 600 |

Performance of Coextruded Film

| Weight (g/m²) | Thickness (mm) | Density (g/cm³) | Tensile Strength (kgf/5 cm) | | Elongation (%) | |
| --- | --- | --- | --- | --- | --- | --- |
| | | | MD | CD | MD | CD |
| 52 | 0.07 | 0.84 | 1.9 | 1.1 | 580 | 602 |

Joining and Drawing of Elastic Body Sheet and Nonwoven Fabric Having Easily Extensible Property According to a process as shown in FIG. 40, the above-mentioned elastic material sheet was drawn to 2.5 times the natural length thereof in the machine direction. The above-mentioned non-woven fabric having an easily stretchable property was laminated onto the surface of the Ra layer, while the elastic sheet was maintained in a drawn state. Then, the elastic sheet was passed between a chrome plated roller and a silicone rubber roller at a linear pressure of about 10 kg/cm to joint the elastic sheet to the non-woven fabric.

The rollers have an embossed pattern as shown in FIG. 27. The surfaces of the rollers were heated at a temperature of about 1200° C. The heat was applied to the non-woven fabric.

After jointing, the elastic sheet and the non-woven fabric were restored to a relaxed state to produce a composite elastic material which has a two-layer structure having creepy corrugations in the machine direction. This composite elastic material was easily elongated in the machine direction, but showed some resistance against elongating in the cross direction. Furthermore, when the composite elastic material was predrawn by about 150% in a cross direction, it became very stretchable in both the machine and cross directions. The elastic properties are shown as follows:

TABLE 2

Performance of Two-Layer Composite Elastic Material

|  | Tensile Strength (kgf/5 cm) | Elongation (%) | Elasticity (g/5 cm) | | | Residual Strain (%) |
| --- | --- | --- | --- | --- | --- | --- |
|  |  |  | 50% | 100% | 150% |  |
| MD | 7.5 | 275 | 90 | 95 | 105 | 15 |
| CD | 1.8 | 400 | 120 | 160 | 180 | 22 |
|  |  | (First Stage 230) |  |  |  |  |

When the two-layer composite elastic material was elongated in a machine direction, the non-woven fabric was fractured, and approximately simultaneously the elastic material was broken. The composite elastic material had a first stress-lowering point and a second stress-lowering point at about 230% in the cross machine direction.

As can be appreciated from the foregoing disclosure, as the composite elastic material of the preferred embodiments is elongated until the breaking limit, the stress approaches the maximum just before the breaking limit. Then, when the composite elastic material is further elongated, the stress reaches a first stress-lowering point which is caused by the breaking of the non-woven fabric. At this point, the stress rapidly decreases, and thereafter, the composite elastic material is elongated with less stress until it reaches the breaking limit of the elastic material. Moreover, if the composite elastic material is elongated but not broken, it can be restored to the original length due to the elastic property of the elastic material. Due to such elongation properties, the composite elastic material of the present invention provides excellent stretch-recovery. Moreover, the composite elastic material has a pleasantly soft feeling to the touch. Thus, the composite elastic material can be advantageously used in a multitude of applications, including, an elastic material applied to parts which directly touch the skin, such as an elastic material which is provided for the sleeve portion of a medical gown, or as an elastic element in the waist or crotch region of sanitary articles.

While the present invention has been described in connection with the preferred embodiments, it will be appreciated by those skilled in the art that various changes may be made to the preferred embodiments without departing from the scope of the invention as defined by the appended claims.

What is claimed is:

1. A composite elastic material having a multiple-stage elongation property comprising:
  a non-woven fabric which is stretchable along at least one direction and has a break-down elasticity along said direction of about 100% or more; and
  a sheet-like elastic member having an elastic recovery of about 60% or more and a break-down elasticity of about 200% or more;

said non-woven fabric and said elastic member being secured together at a plurality of points to form a composite elastic material having a first stress lowering point caused by changes of structure of said non-woven fabric while being stretched along said direction, and a second stress lowering point occurring at an elongation larger than that of said first stress lowering point caused by a break-down of said sheet-like elastic member.

2. The composite elastic material claimed in claim 1, wherein the breakdown elasticity of said non-woven fabric is about 150% or more, and the break-down elasticity of said elastic member is about 250% or more, and the difference in the break-down elasticity between said non-woven fabric and said elastic member is about 100% or more.

3. The composite elastic material claimed in claim 2, wherein the break-down elasticity of said non-woven fabric is about 200% or more.

4. The composite elastic material claimed in claim 1, wherein the difference in elongation between said first and second stress lowering points is about 50% or more.

5. The composite elastic material of claim 1, said composite stretchable in both the longitudinal and transverse directions and having said first and second stress lowering points while being stretched along the longitudinal or transverse directions thereof.

6. The composite elastic material of claim 1, said non-woven fabric selected from a group consisting of a spun-bond non-woven fabric and a melt-blown non-woven fabric.

7. The composite elastic material of claim 1, said non-woven fabric manufactured through water entanglement and having a dual stage elongation of different stress levels.

8. The composite elastic material of claim 7, the second stage elongation of said non-woven fabric occurs when stretched over about 150% or more.

9. The composite elastic material of claim 1, wherein said non-woven fabric has an increased elongation in the cross-machine direction due to its high degree of fibers oriented in the machine direction by hot stretching along the machine direction.

10. The composite elastic material of claim 1, said non-woven fabric comprising an easily fusible material.

11. The composite elastic material of claim 1, wherein said non-woven fabric is a composite non-woven fabric comprising a thermoplastic bonding component and a skeleton component having a higher melting point than said bonding component, said composite non-woven fabric manufactured by stretching said composite non-woven fabric at a temperature exceeding the plasticizing temperature of said bonding component, but less than the melting point of said skeleton component, said composite non-woven fabric having an elongation of 100% or more in the direction perpendicular to said stretching direction.

12. The composite elastic material of claim 11, said composite non-woven fabric comprising a highly random filament non-woven fabric having a strength ratio MD/CD of below about 3.0.

13. The composite elastic material of claim 11, wherein said composite non-woven fabric comprises a spun-bond comprising conjugate fibers consisting of a sheath of polyethylene and a core of polyester, wherein the content of polyethylene is about 40% or more.

14. The composite elastic material of claim 11, said non-woven fabric comprising a core layer of unbonded spun-bond and at least one layer of melt-blown thermoplastic resin disposed on one of the upper and lower surfaces thereof.

15. The composite elastic material of claim 11, said composite non-woven fabric comprising a layer of opened, unbonded filaments and a layer of fibril thermoplastic resin laminated on the upper and lower surfaces thereof.

16. The composite elastic material of claim 11, wherein said sheet-like elastic member comprises an easily fusible material.

17. The composite elastic material of claim 1, wherein said sheet-like elastic member is selected from a group consisting of elastic member urethane or rubber latex; synthetic rubber film of isoprene or butadiene; a styrene elastomer film of SIS, SEBS, or SEPS; a polyolefin elastomer film of EVA, EMA, or EPDM; and a melt-blown elastomer non-woven fabric of polyurethane, SIS, or SEBS.

18. The composite elastic material of claim 1, said non-woven fabric being disposed on and secured to both sides of said sheet-like elastic member.

19. The composite elastic material of claim 18, wherein a first of said non-woven fabrics is disposed on one surface of said elastic member and a second of said non-woven fabrics is disposed on the other surface of said elastic member, said first and said second non-woven fabrics being secured to said elastic member at a plurality of spot points, and said points between said first non-woven fabric and said elastic member being disposed in a manner to avoid overlapping with said points between said second non-woven fabric and said elastic member.

20. The composite elastic material of claim 19, wherein each of said points connecting said sheet-like elastic member and said non-woven fabric extends in a direction perpendicular to the elongation direction of said non-woven fabric.

21. The composite elastic material of claim 1, further comprising two elastic members each of which is secured to said non-woven fabric, said elastic members being secured together to form a four-layered laminate.

22. The composite elastic material of claim 21, wherein one of said non-woven fabric is hydrophilic and the other of said non-woven fabric is hydrophobic.

23. The composite elastic material of claim 21, said non-woven fabric and said elastic member being secured at random spot points.

24. The composite elastic material of claim 23, wherein said points connecting said sheet-like elastic member and said non-woven fabric are disposed in a plurality of rows extending in a direction perpendicular to the elongation direction of said non-woven fabric.

25. The composite being elastic material of claim 24, said composite stretchable in a specific direction by heating and compressing at least one portion thereof at a temperature higher than the melting temperature of said sheet-like elastic member and lower than the melting temperature of said non-woven fabric, thereby forming at least one portion having smaller elongation than that of the remaining portion.

26. The composite elastic material of claim 25, wherein each of said portion having smaller elongation is formed as a strip.

27. The composite elastic material of claim 1, said sheet-like elastic member and said non-woven fabric being secured at selected securement portions, one or more of said securement portions having lower elongation compared to that of an unsecured portion thereof.

28. The composite elastic material of claim 27, wherein said portions having smaller elongation are formed as strip-like securements disposed in parallel.

29. The composite elastic material of claim 27, further comprising a pair of securement portions having smaller elongation disposed at both sides of said composite elastic material.

30. A method of manufacturing a composite elastic material having a multiple-stage elongation comprising the steps of:

placing a non-woven fabric having an elongation along at least one direction and a break-down elasticity along said direction of about 100% or more on a sheet-like elastic member having an elastic recovery of about 60% or more and a break-down elasticity of about 200% or more;

securing said non-woven fabric and said elastic member together at a plurality of discontinuous securements to form a composite material; and drawing said composite material in a stretchable direction of said non-woven fabric with an elongation degree smaller than the break-down elasticity of said elastic member to have a first stress lowering point caused by changes of structure of said non-woven fabric and a second stress lowering point occurring at an elongation larger than that of said first stress lowering point caused by break-down of said sheet-like elastic member.

31. The method claimed in claim 30, wherein said drawing is conducted at an elongation of about 40%–80% of the break-down elasticity of said non-woven fabric.

* * * * *